United States Patent [19]

Hipskind

[11] Patent Number: 5,607,947
[45] Date of Patent: Mar. 4, 1997

[54] PYRROLIDINYL TACHYKININ RECEPTOR ANTAGONISTS

[75] Inventor: Philip A. Hipskind, New Palestine, Ind.

[73] Assignee: Eli Lilly and Company, Indianapolis, Ind.

[21] Appl. No.: 391,814

[22] Filed: Feb. 21, 1995

[51] Int. Cl.⁶ .................... A61K 31/445; C07D 401/14
[52] U.S. Cl. ............................................ 514/316; 546/187
[58] Field of Search ..................... 546/187, 208; 514/316, 320

[56] References Cited

U.S. PATENT DOCUMENTS 5,340,822  8/1994  Emonds-Alt ............................ 514/316
5,472,978  12/1995  Baker ...................................... 514/443

OTHER PUBLICATIONS

Vaught, J L (1988) Life Sci. 43 pp. 1419–1431.

*Primary Examiner*—C. Warren Ivy
*Assistant Examiner*—Evelyn Huang
*Attorney, Agent, or Firm*—Paul J. Gaylo; David E. Boone

[57] ABSTRACT

This invention provides a novel series of substituted pyrrolidines which are useful in the treatment or prevention of a physiological disorder associated with an excess of tachykinins. This invention also provides methods for the treatment of such physiological disorders as well as pharmaceutical formulations which employ these novel compounds.

14 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Phe  Xaa  Gly  Leu  Met
    1                         5

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:2:

```
Arg Pro Lys Pro Gln Gln Phe Phe Gly Leu Met
 1               5                       10
```

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (x i) SEQUENCE DESCRIPTION: SEQ ID NO:3:

```
His Lys Thr Asp Ser Phe Val Gly Leu Met
 1               5                   10
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (x i) SEQUENCE DESCRIPTION: SEQ ID NO:4:

```
Asp Met His Asp Phe Phe Val Gly Leu Met
 1               5                   10
```

PYRROLIDINYL TACHYKININ RECEPTOR ANTAGONISTS

BACKGROUND OF THE INVENTION

Tachykinins are a family of peptides which share the common amidated carboxy terminal sequence, Phe-Xaa-Gly-Leu-Met-$NH_2$ hereinafter referred to as SEQ ID NO:1. Substance P was the first peptide of this family to be isolated, although its purification and the determination of its primary sequence did not occur until the early 1970's. Substance P has the following amino acid sequence, Arg-Pro-Lys-Pro-Gln-Gin-Phe-Phe-Gly-Leu-Met-$NH_2$ hereinafter referred to as SEQ ID NO:2.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries. Neurokinin A has the following amino acid sequence, His-Lys-Thr-Asp-Ser-Phe-Val-Gly-Leu-Met-$NH_2$ hereinafter referred to as SEQ ID NO:3. The structure of neurokinin B is the amino acid sequence, Asp-Met-His-Asp-Phe-Phe-Val-Gly-Leu-Met-$NH_2$ hereinafter referred to as SEQ ID NO:4.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

Recent publications have described novel classes of non-peptidyl tachykinin receptor antagonists which generally have greater oral bioavailability and metabolic stability than the earlier classes of tachykinin receptor antagonists. Examples of such, newer non-peptidyl tachykinin receptor antagonists are found in European Patent Publication 591, 040 A1, published Apr. 6, 1994; Patent Cooperation Treaty publication WO 94/01402, published Jan. 20, 1994; Patent Cooperation Treaty publication WO 94/04494, published Mar. 3, 1994; and Patent Cooperation Treaty publication WO 93/011609, published Jan. 21, 1993.

SUMMARY OF THE INVENTION

This invention encompasses methods for the treatment or prevention of a physiological disorder associated with an excess of tachykinins, which method comprises administering to a mammal in need of said treatment an effective amount of a compound of Formula I

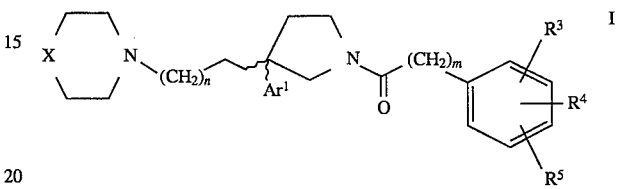

wherein:

n is 0–6;

m is 0–6;

X is

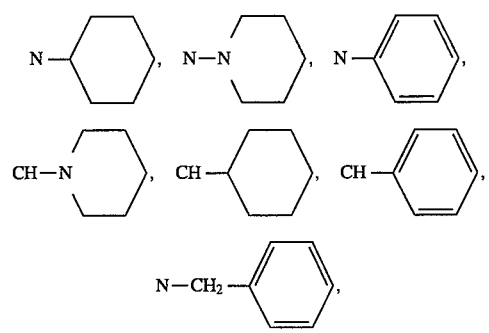

N—$R^a$, or CH—$NR^bR^c$, where $R^a$, $R^b$, and $R^c$ are independently selected from the group consisting of hydrogen and $C_1$–$C_6$ alkyl;

$Ar^1$ is phenyl substituted with one, two, or three moieties independently selected from the group consisting of hydrogen, halo, trifluoromethyl, trichloromethyl, $C_1$–$C_6$ alkyl, and $C_1$–$C_6$ alkoxy; or $Ar^1$ is naphthyl; and $R^3$, $R^4$, and $R^5$ are independently selected from the group consisting of hydrogen, halo, trifluoromethyl, $C_1$–$C_6$ alkyl, $C_1$–$C_6$ alkoxy, cyano, hydroxy, amino, —NHCON$H_2$, nitro, —CON$H_2$, $C_2$–$C_{10}$ alkenyl, $C_2$–$C_{10}$ alkynyl, $C_3$–$C_8$ cycloalkyl, $C_3$–$C_8$ cycloalkenyl, $C_3$–$C_8$ cycloalkoxy, $C_1$–$C_{10}$ alkylthio, $C_1$–$C_{10}$ alkylamino, $C_2$–$C_6$ alkanoyl, and $C_2$–$C_6$ alkanoyloxy.

or a pharmaceutically acceptable salt or solvate thereof.

In other embodiments this invention encompasses the novel compounds of Formula I and the salts and solvates of those compounds, as well as pharmaceutical formulations comprising at least one compound of Formula I, or a pharmaceutically acceptable salt or solvent of said compound, in combination with one or more pharmaceutically acceptable carrier, diluents, or excipients.

DETAILED DESCRIPTION AND PREFERRED EMBODIMENTS

The terms and abbreviations used in the instant examples have their normal meanings unless otherwise designated.

For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_{10}$ alkyl" refers to straight or branched, monovalent, saturated aliphatic chains of 1 to 10 carbon atoms and includes, but is not limited to, methyl, ethyl, propyl, isopropyl, butyl, isobutyl, t-butyl, pentyl, isopentyl, and hexyl. The term "$C_1$–$C_{10}$ alkyl" includes within its definition the terms "$C_1$–$C_6$ alkyl" and "$C_1$–$C_3$ alkyl".

"Halo" represents chloro, fluoro, bromo or iodo.

"$C_1$–$C_{10}$ alkylthio" represents a straight or branched alkyl chain having from one to ten carbon atoms attached to a sulfur atom. Typical $C_1$–$C_{10}$ alkylthio groups include methylthio, ethylthio, propylthio, isopropylthio, butylthio and the like. The term "$C_1$–$C_{10}$ alkylthio" includes within its definition the term "$C_1$–$C_6$ alkylthio" and "$C_1$–$C_3$ alkylthio".

The term "$C_2$–$C_{10}$ alkenyl" as used herein represents a straight or branched, monovalent, unsaturated aliphatic chain having from two to ten carbon atoms. Typical $C_2$–$C_{10}$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

The term "$C_2$–$C_{10}$ alkynyl" as used herein represents a straight or branched, monovalent, unsaturated aliphatic chain having from two to ten carbon atoms with at least one triple bond. Typical $C_2$–$C_{10}$ alkynyl groups include ethynyl, 1-methylethenyl, 1-propynyl, 1-butynyl, 1-hexynyl, 2-propynyl, 2-butynyl, 2-pentynyl, and the like.

"$C_3$–$C_8$ cycloalkenyl" represents a hydrocarbon ring structure containing from three to eight carbon atoms and having at least one double bond within that ring, which is unsubstituted or substituted with 1, 2 or 3 substituents independently selected from halo, halo($C_1$–$C_4$ alkyl), $C_1$–$C_4$alkyl, $C_1$–$C_4$ alkoxy, carboxy, $C_1$–$C_4$ alkoxycarbonyl, carbamoyl, N-($C_1$–$C_4$ alkyl)carbamoyl, amino, $C_1$–$C_4$ alkylamino, di($C_1$–$C_4$ alkyl)amino or —$(CH_2)_a$—$R^y$ where a is 1, 2, 3 or 4 and $R^y$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$ alkyl)amino.

"$C_1$–$C_6$ alkylamino" represents a straight or branched alkylamino chain having from one to six carbon atoms attached to an amino group. Typical $C_1$–$C_6$ alkyl-amino groups include methylamino, ethylamino, propylamino, isopropylamino, butylamino, sec-butylamino and the like. "$C_1$–$C_6$ alkylamino" encompasses within this term "$C_1$–$C_4$ alkylamino".

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_3$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_2$–$C_6$ alkanoyloxy" represents a straight or branched alkyl chain having from one to five carbon atoms attached to a carbonyl moiety joined through an oxygen atom. Typical $C_2$–$C_6$ alkanoyloxy groups include acetoxy, propanoyloxy, isopropanoyloxy, butanoyloxy, t-butanoyloxy, pentanoyloxy, hexanoyloxy, 3-methylpentanoyloxy and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxy-carbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, PROTECTIVE GROUPS IN ORGANIC SYNTHESIS, (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, Supra, at Chapter 5, and T. W. Greene, et al,, supra, at Chapter 5.

The term "hydroxy-protecting groups" as used herein refers to substitents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, x-9965-10 adamantoate and tetrahydropyranyl. Further examples of these groups may be found in T. W. Greene and P. G. M. Wuts, PROTECTIVE GROUPS IN ORGANIC SYNTHESIS, (1991) at Chapter 3.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

The term "haloformate" as used herein refers to an ester of a haloformic acid, this compound having the formula

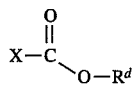

wherein X is halo, and $R^d$ is $C_1$–$C_6$ alkyl. Preferred haloformates are bromoformates and chloroformates. Especially preferred are chloroformares. Those haloformates wherein $R^d$ is $C_3$–$C_6$ are preferred. Most preferred is isobutyl chloroformate.

The compounds used in the method of the present invention may have one or more asymmetric centers. As a consequence of these chiral centers, the compounds of the present invention may occur as racemates, mixtures of enantiomers and as individual enantiomers, as well as diastereomers and mixtures of diastereomers. All asymmetric forms, individual isomers and combinations thereof, are within the scope of the present invention.

The designation "⌇" refers to a bond for which the stereochemistry is not designated.

The terms "R" and "S" are used herein as commonly used in organic chemistry to denote specific configuration of a chiral Center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al., "Enantiomers, Racemates, and Resolutions", (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quarternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solyates of the compounds of Formulas I. Many of the Formula I compounds can combine with a solvent such as water, methanol, ethanol or acetonitrile to form a pharmaceutically acceptable solvate such as the corresponding hydrate, methanolate, ethanolate or acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:

1) ester or amide derivatives which may be cleaved by esterases or lipases;

2) peptides which may be recognized by specific or nonspecific proteases; or 3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, Design of Prodrugs, (1985).

The especially preferred compounds of this invention are those compounds wherein:

a) $Ar^1$ is phenyl substituted with one or two moieties independently selected from the group consisting of chloro, fluoro, bromo, methyl, ethyl, isopropyl, methoxy, ethoxy, isopropoxy, trichloromethyl, and trifluoromethyl;

b) $R^3$, $R^4$ and $R^5$ are independently selected from the group consisting of hydrogen, chloro, fluoro, bromo, trifluoromethyl, methyl, ethyl, isopropyl, methoxy, ethoxy, isopropoxy, amino, —$NHCONH_2$, —$CONH_2$, vinyl, propenyl, methylthio, ethylthio, isopropylthio, methylamino, ethylamino, dimethylamino, acetyl, and acetoxy, with the proviso that at least one of $R^3$, $R^4$ and $R^5$ is hydrogen unless all of $R^3$, $R^4$ and $R^5$ are chloro, fluoro, bromo, trifluoromethyl, methyl, ethyl, methoxy, or ethoxy;

c) n is 0, 1, or 2;

d) m is 0, 1, or 2; and d) X, when combined to the heterocyclic group to which it is attached, forms 4-(cyclohexyl)piperazin-1-yl, 4-(piperidin-1-yl)piperidin-1-yl, 4-dimethylaminopiperidin-1-yl, 4-phenylpiperazin-1-yl, or 4-benzylpiperazin-1-yl.

The compounds of the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

The term "optionally in the presence of a base" indicates that the reaction may be performed with a base present, but such a base is not required for the reaction to proceed. Preferred bases include organic bases containing one or more nitrogen groups, such as N-methylmorpholine, ethylamine, diethylamine, triethylamine, ethyldiisopropylamine, pyridine, and the like. Especially preferred are N-methylmorpholine and pyridine. The absence of a base is usually most preferred.

The compounds of Formula I may be prepared by a variety of means known to those skilled in the art. A preferred method of preparing the compounds of Formula I comprises treating a compound of Formula II

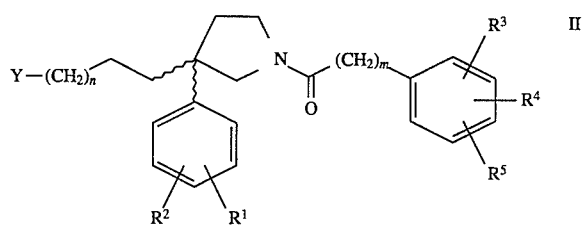

where $R^1$ and $R^2$ are independently hydrogen, halo, trifluoromethyl, trichloromethyl, $C_1$–$C_6$ alkyl, or $C_1$–$C_6$ alkoxy, and Y is any leaving group, preferably a mesyl, tosyl, or benzenesulfonyl group, or a protected derivative thereof, with a compound of Formula III

in an organic solvent, at a temperature between −78° C. and 120° C., and isolating the resulting product. The organic solvent used is preferably a polar aprotic solvent, for example, acetonitrile, N,N-dimethylformamide, N,N-dimethylphenylacetamide, dimethylsulfoxide, or hexamethylphosphoric triamide. Instead of using a polar aprotic solvent it is also possible to use an ether, such as tetrahydrofuran, dioxane, or methyl t-butyl ether, or a ketone, such as methyl ethyl ketone. Acetonitrile is the most preferred solvent.

In the temperature range indicated above, the preferred temperature is 70°–90° C. If acetonitrile is employed as a solvent, the reaction is advantageously carried out at the reflux point of the reaction mixture.

The product obtained in this way is isolated by the usual techniques, for example, by concentration of the solvents, followed by washing of the residue with water, and then purification by conventional techniques, such as chromatography or recrystallization.

The derivatives of Formula II, used as a reactant in the preparation of the compounds of Formula I, may be prepared as described in Scheme I, infra. In Scheme I the reactions in the various steps are shown in a representative way so as to indicate the type of said reactions without giving the means employed, which are known.

Scheme I

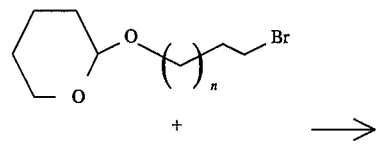

a)

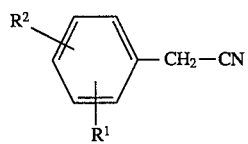

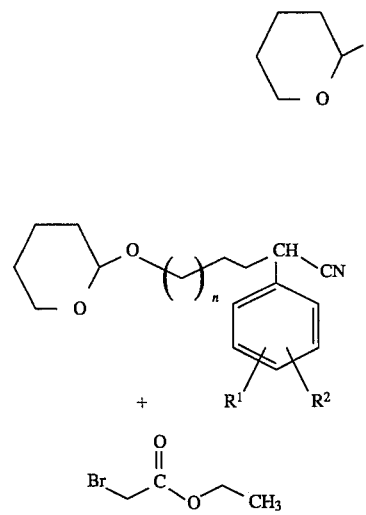

b)

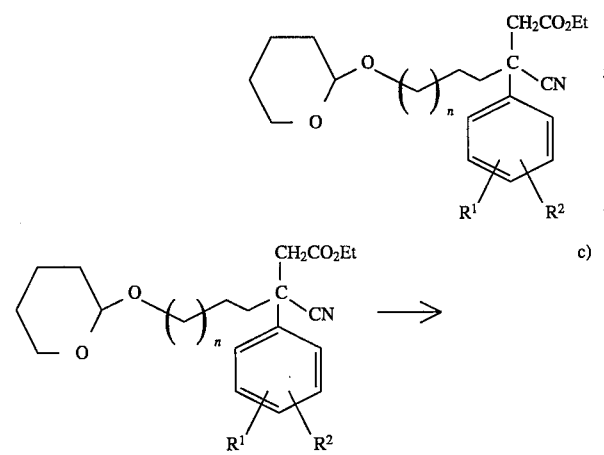

-continued
Scheme I

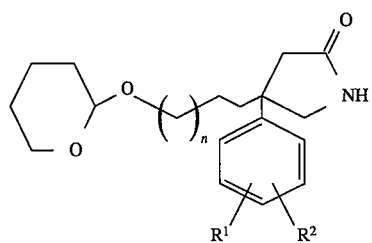

d)

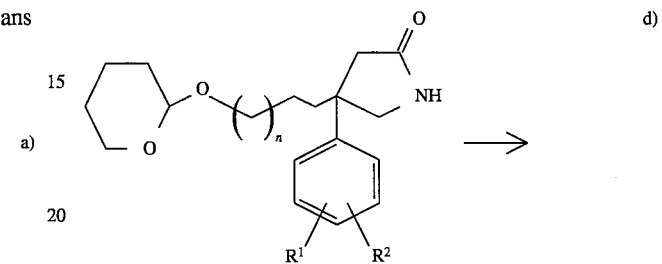

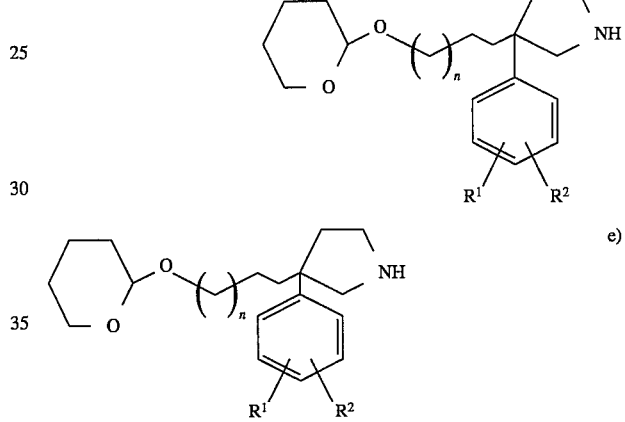

e)

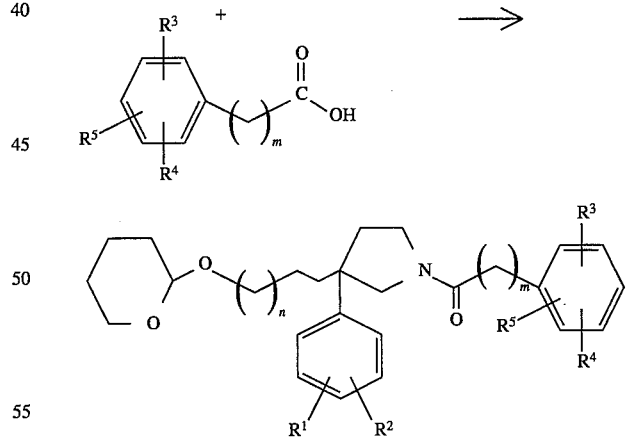

f)

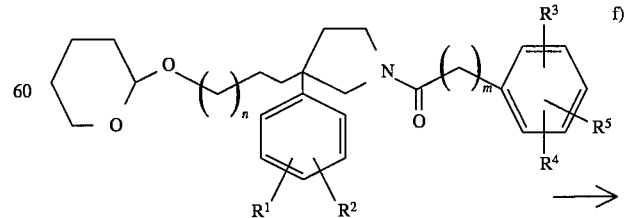

11
-continued
Scheme I

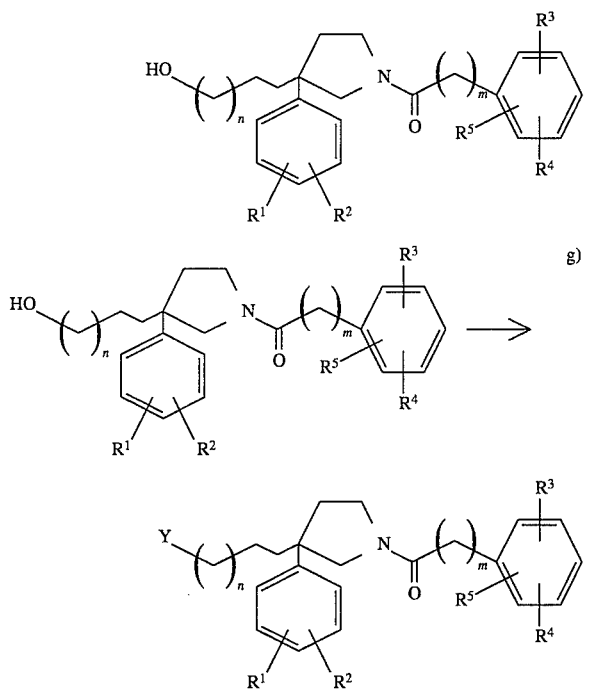

This reaction scheme involves a series of reactions well known to those skilled in the art, such as the alkylation of a nitrile with a brominated derivative in the presence of lithium diisopropylamide (LDA) (step b) followed by reduction of the nitrile, optionally in the presence of a catalyst, to give the corresponding amine after reduction of the intermediate amide (Step d) obtained during the cyclization (Step c), for example according to A. V. El'Tsov, et al., *Biol. Soedin., Akad. Nauk. SSSR*, 109–112 (1965), abstracted in, *Chemical Abstracts*, 63:16299 (1965).

The coupling of the substituted pyrrolidine and the acid (Step e) is performed in the presence of a coupling agent, by the usual methods. It is also possible to use a functional derivative of this acid, such as the acid itself appropriately activated by cyclohexylcarbodiimide or by benzotriazolyl-N-oxytrisdimethylaminophosphonium hexafluorophosphate (BOP), for example, or else one of the functional derivatives which react with amines, for example, an anhydride, a mixed anhydride, the acid chloride, or an activated ester such as the p-nitrophenyl ester.

The alcohol resulting from the deprotection (Step f) is then reacted with an activating agent, such as mesyl chloride, tosyl chloride, or benzenesulfonyl chloride (Step g) to afford the compound of Formula II.

During any of the above synthetic sequences it may be necessary or desirable to protect sensitive or reactive amino, hydroxy, or carboxy groups on any of the molecules concerned. Such protection may be accomplished by means of the amino-protecting, hydroxy-protecting, or carboxy-protecting groups discussed supra. These protecting groups may be removed at a convenient subsequent stage using methods known in the art.

Those compounds of Formula I or II wherein $Ar^1$ is naphthyl may be prepared substantially as described above except that the corresponding naphthylacetonitrile is employed instead of the benzeneacetonitrile described above.

The following Preparations and Examples further illustrate the compounds of the present invention and the methods for their synthesis. The Preparations and Examples are not intended to be limiting to the scope of the invention in any respect, and should not be so construed. All solvents and reagents were purchased from commercial sources and used as received, unless otherwise indicated. Dry tetrahydrofuran (THF) was obtained by distillation from sodium or sodium benzophenone ketyl prior to use.

The starting materials described herein are commercially available or may be prepared by methods well known to those in the art.

Preparation 1

Preparation of 3-(2-hydroxyethyl)-3-(3,4-dichlorophenyl)pyrrolidine (i) Ethyl γ-(2-tetrahydropyranyloxethyl)-γ-cyano-γ-(3,4-dichlorophenyl)propanoate Twenty-two grams of a 55–60% dispersion of sodium hydride in oil are suspended in 200 ml of dry tetrahydrofuran. A solution of 85 g of 3,4-dichlorophenylacetonitrile in 500 ml of tetrahydrofuran is added dropwise at 20° C. over 30 minutes and the reaction mixture is then stirred at room temperature for about two hours. A solution of 98 grams of 2-bromoethoxytetrahydropyran in 100 ml of tetrahydrofuran is added to the reaction mixture cooled to −20° C., the mixture is allowed to warm up to room temperature, and, after two hours, a solution of 50 grams of ammonium chloride in three liters of water is added. Extraction is carried out with 1.5 liters of ethyl ether and the extract is washed with a saturated solution of sodium chloride, decanted, dried over magnesium sulfate, and concentrated under vacuum. The residue is chromatographed on silica gel using dichloromethane as the eluent. The pure product fractions are concentrated to give 3,4-dichloro-α-(2tetrahydropyranyloxyethyl)benzeneacetonitrile as an oil.

The 3,4-dichloro-α-(2-tetrahydropyranyloxyethyl)benzeneacetonitrile, prepared above (21 grams) is dissolved in 100 ml of tetrahydrofuran, a solution of 0.067 ml of lithium diisopropylamine in 100 ml of tetrahydrofuran is then added dropwise at room temperature, and the reaction mixture is stirred for one hour at room temperature. Ethyl bromoacetate (12 g) is then added and the mixture is heated to 50° C. for two hours. The mixture is cooled, poured into a saturated solution of ammonium chloride, and extracted with diethyl ether. The extract is washed with water and the ether phase is removed by decantation, dried over sodium sulfate, and concentrated in vacuo.

The residue is purified by chromatography on silica gel using dichloromethane/ethyl acetate (100/1 v/v) as the eluent. The proper fractions are then purified by removal of the solvents in vacuo.

(ii) 3-(2-Tetrahydropyranyloxyethyl)-3-(3,4-dichlorophenyl)-2-pyrrolidinone

The compound prepared in (i) (13 g) is dissolved in 250 ml of ethanol and 40 ml of aqueous ammonia. The reaction mixture is then hydrogenated at room temperature and atmospheric pressure in the presence of Raney nickel. When the theoretical volume of hydrogen has been absorbed, the mixture is filtered on CELITE™ and the filtrate is concentrated under vacuum. The residue is taken up in water and extracted with ether. The organic fraction is then washed with water, dried over magnesium sulfate, and conetrated under vacuum to give the title intermediate.

(iii) 3-(2-Tetrahydropyranyloxyethyl)-3-(3,4-dichlorophenyl)pyrrolidine

The 3-(2-tetrahydropyranyloxyethyl)-3-(3,4-dichlorophenyl)-2-pyrrolidinone (3.9 grams prepared as described supra) is dissolved in 50 ml of tetrahydrofuran and the solution is added to a suspension of 0.9 grams of lithium aluminum hydride in 5 ml of tetrahydrofuran heated to 60° C. The reaction mixture is then heated for one hour at 60° C. and then cooled. To the resulting mixture 1 ml of water, 1 ml of 4N sodium hydroxide, and 3 ml of water are added sequentially. The insoluble portion is removed by filtration and the filtrate is concentrated in vacuo. The residue is taken up in diethyl ether, dried over magnesium sulfate, and concentrated under vacuum to give the desired intermediate.

(iv) 3-(2-Hydroxyethyl)-3-(3,4-dichlorophenyl)pyrrolidine

A saturated solution of hydrogen chloride in diethyl ether is added to a solution of 55 grams of 3-(2-tetrahydropyranyloxyethyl)-3-(3,4dichlorophenyl)pyrrolidine in 200 ml of methanol until the pH is 1.0. The mixture is stirred for about thirty minutes at room temperature and concentrated to dryness. The residue is then taken up in water, rendered alkaline with a solution of sodium hydroxide and extracted with methylene chloride. The extract is then washed with a saturated solution of sodium chloride, dried over sodium sulfate, and evaporated to dryness to give an oil. The oil is taken up in 200 ml of an isopropyl ether/diethyl ether mixture (50/50). After stirring and filtration, the desired intermediate is washed with ethyl ether and dried over phosphorous pentoxide.

(v) (+) 3-(2-Hydroxyethyl)-3-(3,4-dichlorophenyl)pyrrolidine

A solution of 23.54 grams of L(+)-tartaric acid in 750 ml of 100° C. ethanol is added to a refluxing solution of 43 grams of the product obtained above in 200 ml of 100° C. The reaction mixture is refluxed for about thirty minutes, and allowed to cool to room temperature. The crystals obtained are filtered off, washed with 100° C. ethanol and dried under vacuum over phosphorous pentoxide to give the tartrate salt.

After recrystallization from 540 ml of 100° C. and filtration, the tartrate is washed with diethyl ether and dried under vacuum over phosphorous pentoxide to give the tartrate. The tartrate is then taken up in water, neutralized with a solution of sodium hydroxide, and extracted with methylene chloride. The extract is then washed with water, dried over sodium sulfate, and evaporated to dryness. The oil is taken up in a diethyl ether/isopropyl ether mixture and the crystals are filtered off, washed with diethyl ether, and dried under vacuum at 50° C. to give the title intermediate.

(vi) (−) 3-(2-Hydroxyethyl)-3-(3,4-dichlorophenyl)pyrrolidine

The (−) enantiomer is obtained by following the above procedure starting from D(−)-tartaric acid.

Preparation 2

Preparation of 3-(2-hydroxyethyl)-3-[3,4-bis(trifluoromethyl)phenyl]pyrrolidine

The title compound is prepared essentially as described in Preparation 1 except that 3,4-bis(trifluoromethyl)phenylacetonitrile is employed as a starting material in place of 3,4-dichlorophenylacetonitrile.

Preparation 3

Preparation of 3-(2-hydroxyethyl)-3-(3,4-dimethylphenyl)pyrrolidine

The title compound is prepared essentially as described in Preparation 1 except that 3,4-dimethylphenylacetonitrile is employed as a starting material in place of 3,4-dichlorophenylacetonitrile.

Preparation 4

Preparation of 3-(2-hydroxyethyl)-3-(4-methylphenyl)pyrrolidine

The title compound is prepared essentially as described in Preparation 1 except that 4-methylphenylacetonitrile is employed as a starting material in place of 3,4-dichlorophenylacetonitrile.

Preparation 5

Preparation of 3-(2-hydroxyethyl)-3-(3,4-dimethoxyphenyl)pyrrolidine

The title compound is prepared essentially as described in Preparation 1 except that 3,4-dimethoxyphenylacetonitrile is employed as a starting material in place of 3,4-dichlorophenylacetonitrile.

Preparation 6

Preparation of 3-(2-hydroxyethyl)-3-(3-chlorophenyl)pyrrolidine

The title compound is prepared essentially as described in Preparation 1 except that 3-chlorophenylacetonitrile is employed as a starting material in place of 3,4-dichlorophenylacetonitrile.

Preparation 7

Preparation of 3-(2-hydroxyethyl)-3-(3,4-difluorophenyl)pyrrolidine

The title compound is prepared essentially as described in Preparation 1 except that 3,4-difluorophenylacetonitrile is employed as a starting material in place of 3,4-dichlorophenylacetonitrile.

Preparation 8

Preparation of 3-(2-hydroxyethyl)-3-(2,5-dimethylphenyl)pyrrolidine

The title compound is prepared essentially as described in Preparation 1 except that 2,5-dimethylphenylacetonitrile is employed as a starting material in place of 3,4-dichlorophenylacetonitrile.

Preparation 9

Preparation of 3-(2-hydroxyethyl)-3-(2,5-diethoxyphenyl)pyrrolidine

The title compound is prepared essentially as described in Preparation 1 except that 2,5-diethoxyphenylacetonitrile is employed as a starting material in place of 3,4-dichlorophenylacetonitrile.

Preparation 10

Preparation of 3-(2-hydroxyethyl)-3-[3,4-bis(trichloromethyl)phenyl]pyrrolidine

The title compound is prepared essentially as described in Preparation 1 except that 3,4-bis(trichloromethyl)phenylacetonitrile is employed as a starting material in place of 3,4-dichlorophenylacetonitrile.

Preparation 11

Preparation of 3-isopropoxyphenylacetic acid.

(i) Ethyl 3-hydroxyphenylacetate.

A solution of 55 grams of 3-hydroxyphenylacetic acid in 400 ml of 100° C. ethanol is refluxed overnight in the presence of a few drops of concentrated sulfuric acid. It is then evaporated to dryness and the residue is taken up in diethyl ether and washed with water, and then with a saturated aqueous solution of sodium bicarbonate. After drying over magnesium sulfate, followed by evaporation, the desired title intermediate is obtained as an oil.

(ii) Ethyl 3-isopropoxyphenylacetate

A solution of 58 grams of the product obtained above, 88 grams of potassium carbonate, and 108 grams of 2-iodopropane in 300 ml of N,N-dimethylformamide is heated at 80°–100° C. for eight hours. The solvent is removed by evaporation and the residue is taken up in ethyl acetate and washed with a 10% aqueous solution of potassium carbonate. After drying over magnesium sulfate, followed by removal of the solvents in vacuo, the title intermediate is purified by chromatography on silica gel using methylene chloride as the eluent.

(iii) 3-Isopropoxyphenylacetic acid

A solution of 31 grams of the product obtained above and 20 grams of sodium hydroxide in 400 ml of ethanol is refluxed for two hours. The solvents are removed in vacuo and the residue is taken up in water and acidified with concentrated hydrochloric acid. Extraction is carried out with diethyl ether and the extract is washed with water, dried over magnesium sulfate, and concentrated to dryness to give the desired title product.

Preparation 12

Preparation of 5-isopropoxyphenylacetic acid

The title compound is prepared using known methods essentially as described in R. E. Counsel, et al., *Journal of Medicinal Chemistry*, 16:684–687 (1973) except that the benzyl chloride is replaced with 2-iodopropane. The 5-isopropoxyphenylacetonitrile thus prepared (15 grams) is dissolved in 160 ml of ethanol in the presence of 18 grams of potassium hydroxide. The resulting mixture is then refluxed for about two hours. The reaction mixture is then concentrated in vacuo and the residue is taken up in water and washed with diethyl ether. The aqueous phase is acidified with hydrochloric acid until the pH is 1, and extracted with diethyl ether. The extract is washed with water, dried over sodium sulfate, and filtered. The solvents are removed in vacuo and the residue is purified by chromatography on silica gel using methylene chloride/methanol (100/2 v/v) as the eluent to give the desired title product.

Preparation 13

Preparation of 2-fluorophenylacetic acid

The title intermediate is prepared essentially as described in Preparation 12 except that 2-fluorophenylacetonitrile is used as a starting material instead of 2-iodo-5-isopropoxyphenylacetonitrile.

Preparation 14

Preparation of 2-trifluoromethylphenylacetic acid

The title intermediate is prepared essentially as described in Preparation 12 except that 2-trifluoromethylphenylacetonitrile is used as a starting material instead of 2-iodo-5-isopropoxyphenylacetonitrile.

Preparation 15

Preparation of 3,5-bis(trifluoromethyl)phenylacetic acid

The title intermediate is prepared essentially as described in Preparation 12 except that 3,5-bis(trifluoromethyl)phenylacetonitrile is used as a starting material instead of 2-iodo-5-isopropoxyphenylacetonitrile.

Preparation 16

Preparation of 3,4,5-trimethoxyphenylacetic acid

The title intermediate is prepared essentially as described in Preparation 12 except that 3,4,5-trimethoxyphenylacetonitrile is used as a starting material instead of 2-iodo-5-isopropoxyphenylacetonitrile.

Preparation 17

Preparation of 4-nitrophenylacetic acid

The title intermediate is prepared essentially as described in Preparation 12 except that 4-nitrophenylacetonitrile is used as a starting material instead of 2-iodo-5-isopropoxyphenylacetonitrile.

Preparation 17

Preparation of 2-chloro-6-fluorophenylacetic acid

The title intermediate is prepared essentially as described in Preparation 12 except that 2-chloro-6-fluorophenylacetonitrile is used as a starting material instead of 2-iodo-5-isopropoxyphenylacetonitrile.

Preparation 18

Preparation of 4-hydroxyphenylacetic acid

The title intermediate is prepared essentially as described in Preparation 12 except that 4-hydroxyphenylacetonitrile is used as a starting material instead of 2-iodo-5-isopropoxyphenylacetonitrile.

Preparation 19

Preparation of 3-(2-methanesulfonyloxyethyl)-3-(3,4-dichlorophenyl)-1-[(3-isopropoxyphenyl)acetyl]pyrrolidine and 3-(2-benzenesulfonyloxyethyl)-3-(3,4-dichlorophenyl)-1-[(3-isopropoxyphenyl)acetyl]pyrrolidine.

(i) 3-(2-Hydroxyethyl)-3-(3,4-dichlorophenyl)-1-[(3-isopropoxyphenyl)acetyl]pyrrolidine Triethylamine (22.5 ml) and 3-(2-hydroxyethyl)-3-(3,4-dichlorophenyl)pyrrolidine (22 grams) are added to a solution of 16 grams of 3-isopropoxyphenylacetic acid in 500 ml of methylene chloride. The mixture is cooled to 0° C. and 42.6 grams of benzotriazolyl-N-oxytrisdimethylaminophosphonium hexafluorophosphate are then added and the reaction mixture is allowed to warm up to room temperature.

After thirty minutes, the mixture is concentrated under vacuum and the residue is taken up in diethyl ether and washed successively with water, a dilute sodium hydroxide solution, a saturated sodium chloride solution, a dilute hydrochloric acid solution, a saturated sodium chloride solution, and a solution of sodium bicarbonate. The organic fraction is dried over magnesium sulfate, filtered, and concentrated in vacuo to yield the title intermediate.

(ii) 3-(2-Methanesulfonyloxyethyl)-3-(3,4-dichlorophenyl)-1-[(3-isopropoxyphenyl)acetyl]pyrrolidine The product prepared above (36 grams) is dissolved in 500 ml of methylene chloride and the solution is cooled to 0° C. Triethylamine (11.5 ml) is added followed by the dropwise addition of methanesulfonyl chloride (mesyl chloride, 6.3 ml). The reaction mixture is left to stand for about 15 minutes at 0° C. and then concentrated under vacuum. The residue is taken up in diethyl ether and washed with water. The organic fraction is dried over magnesium sulfate, filtered, and concentrated under vacuum. The residue is chromatographed on silica gel using heptane/ethyl acetate (50/50 v/v) up to pure ethyl acetate as the eluent. The pure product fractions are concentrated under vacuum and the residue is then solidified in a diethyl ether/isopropyl ether mixture to give the title product.

(iii) 3-(2-Benzenesulfonyloxyethyl)-3-(3,4-dichlorophenyl)-1-[(3-isopropoxyphenyl)acetyl]pyrrolidine Triethylamine (4.6 ml) is added to 11.3 grams of the product in step (i) in 160 ml of methylene chloride, followed by the dropwise addition of 4.3 ml of benzenesulfonyl chloride. The resulting solution is cooled to 0° C. The reaction mixture is then warmed to room temperature and left to stand for about 18 hours. The reaction mixture is then washed successively with 100 ml of hydrochloric acid, 100 ml of 10% sodium bicarbonate, and 100 ml of water. The organic fraction is removed, dried over sodium sulfate, and then concentrated under vacuum. The residue is chromatographed on silica gel using cyclohexane/ethyl acetate (80/20 v/v) as the eluent to give the title product.

Preparation 20

Preparation of 3-(2-methanesulfonyloxyethyl)-3-(3, 4-dichlorophenyl)-1-[(3-isopropoxybenzoyl)pyrrolidine The title intermediate is prepared essentially as described in Preparation 19, supra, except that an equimolar amount of 3-isopropoxybenzoic acid is employed instead of the 3-isopropoxyphenylacetic acid employed therein.

Preparation 21

Preparation of 3-(2-hydroxyethyl)-3-(1-naphthyl)pyrrolidine

The title compound is prepared essentially as described in Preparation 1, supra, except that an equimolar amount of 1-naphthylacetonitrile is employed instead of the 3,4-dichlorophenylacetonitrile of that preparation.

Preparation 22

Preparation of 3-(2-methanesulfonyloxyethyl)-3-(31-naphthyl)-1-[(3-isopropoxybenzoyl)pyrrolidine The title intermediate is prepared essentially as described in Preparations 19 and 20, Supra, except that 3-(2-hydroxyethyl)-3-(1-naphthyl)pyrrolidine is employed instead of the 3-(2-hydroxyethyl)-3-(3,4-dichlorophenyl)pyrrolidine employed therein.

EXAMPLE 1

Preparation of (S)-3-(3,4-dichlorophenyl)-1-[(3-isopropoxyphenyl)acetyl]-3-[2-[4-(piperidin-1-yl)piperidin-1-yl]ethyl]pyrrolidine

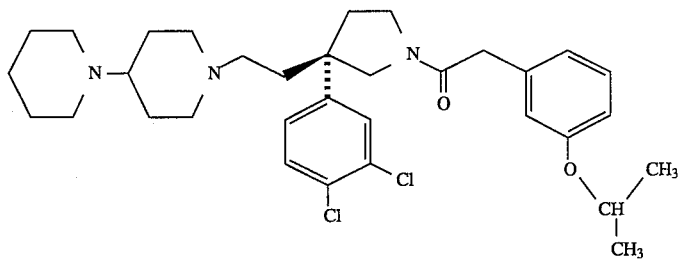

In 30 ml of acetonitrile (S)-3-(2-methanesulfonyloxyethyl)-3-(3,4-dichlorophenyl)-1-[(3-isopropoxyphenyl)acetyl]pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum an the residue is taken up in methylene chloride and washed with a 3 N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 2

Preparation of (S)-3-[3,4-bis(trifluoromethyl)phenyl]-1-[(3-isopropoxyphenyl)acetyl]-3-[2-[4-(piperidin -1-yl)piperidin-1-yl ]ethyl]pyrrolidine

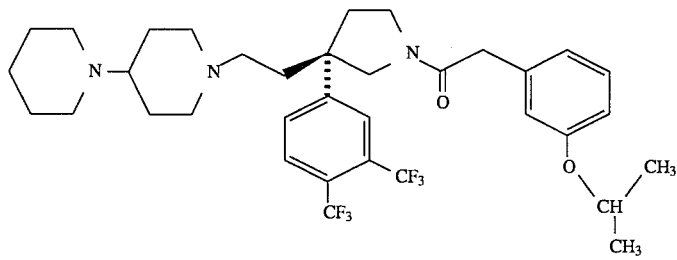

The title compound is prepared essentially as described in Example 1 except that (S)-3-(2-methanesulfonyloxyethyl)-3-[3,4-bis(trifluoromethyl)phenyl]-1-[(3-isopropoxyphenyl)acetyl]pyrrolidine is employed instead of (S)-3-(2-methanesulfonyloxyethyl)-3-(3,4-dichlorophenyl)-1-[(3-isopropoxyphenyl)acetyl]pyrrolidine.

EXAMPLE 3

Preparation of (S)-3-(3,4-dimethylphenyl)-1-[(3-isopropoxyphenyl)acetyl]-3-[2-[4-(piperidin-1-yl)piperidin-1-yl]ethyl]pyrrolidine

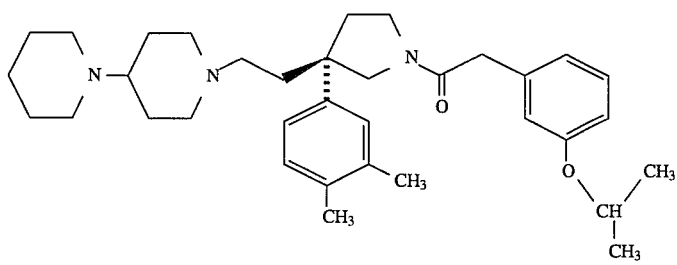

The title compound is prepared essentially as described in Example 1 except that (S)-3-(2-methanesulfonyloxyethyl)-3-(3,4-dimethylphenyl)-1-[(3-isopropoxyphenyl)acetyl]pyrrolidine is employed instead of (S)-3-(2-methanesulfonyloxyethyl)-3-(3,4-dichlorophenyl)-1-[(3-isopropoxyphenyl)acetyl]pyrrolidine.

EXAMPLE 4

Preparation of (S)-3-(4-methylphenyl)-1-[(3-isopropoxyphenyl)acetyl]-3-[2-[4-(piperidin-1-yl)piperidin-1-yl]ethyl]pyrrolidine

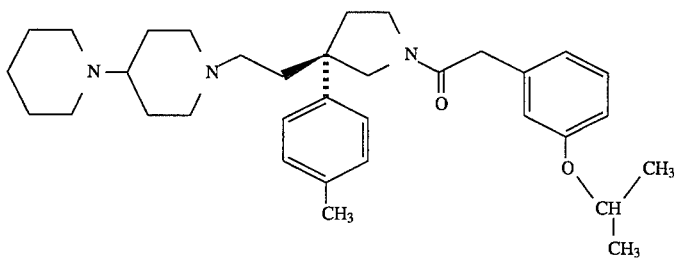

The title compound is prepared essentially as described in Example 1 except that (S)-3-(2-methanesulfonyloxyethyl)-3-(4-methylphenyl)-1-[(3-isopropoxyphenyl)acetyl]pyrrolidine is employed instead of (S)-3-(2-methanesulfonyloxyethyl)-3-(3,4-dichlorophenyl)-1-(3-isopropoxyphenyl)acetyl)piperidine.

EXAMPLE 5

Preparation of (S)-3-(3,4-dimethoxyphenyl)-1-[(3-isopropoxyphenyl)acetyl]-3-[2-[4-(piperidin-1-yl)piperidin-1-yl]ethyl]pyrrolidine

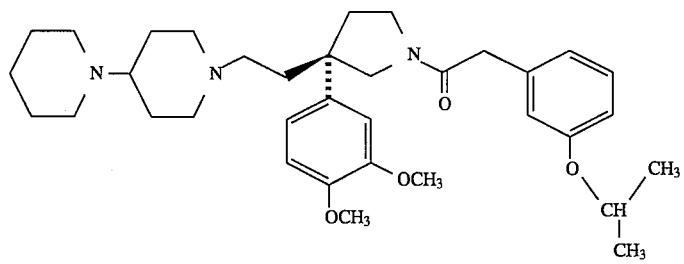

The title compound is prepared essentially as described in Example 1 except that (S)-3-(2-methanesulfonyloxyethyl)-3-(3,4-dimethoxyphenyl)-1-[(3-isopropoxyphenyl)acetyl)pyrrolidine is employed instead of (S)-3-(2-methanesulfonyloxyethyl)-3-(3,4-dichlorophenyl)-1-(3-isopropoxyphenyl)acetyl)pyrrolidine.

EXAMPLE 6

Preparation of (S)-3-(3-chlorophenyl)-1-[(3isopropoxyphenyl)acetyl]-3-[2-[4-(piperidin-1-yl)piperidin-1-yl]ethyl]pyrrolidine

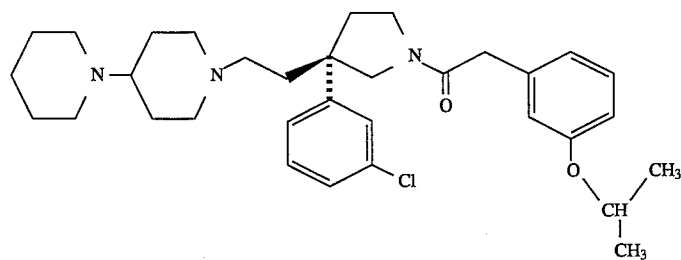

The title compound is prepared essentially as described in Example 1 except that (S)-3-(2-methanesulfonyloxyethyl)-3-(3-chlorophenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 7

Preparation of (S)-3-(3,4-difluorophenyl)-1-[(3-isopropoxyphenyl)acetyl]-3-[2-[4-(piperidin-1-yl)piperidin-1-yl]ethyl]pyrrolidine

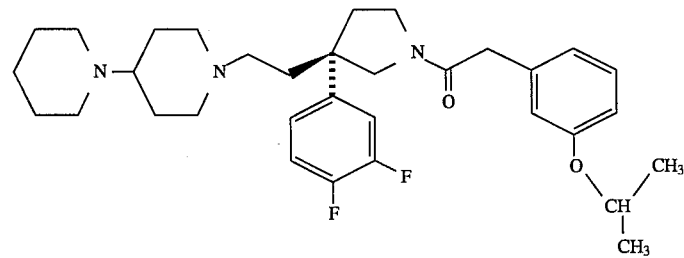

The title compound is prepared essentially as described in Example 1 except that (S)-3-(2-methanesulfonyloxyethyl)-3-(3,4-difluorophenyl)-1-[(3-isopropoxyphenyl)acetyl)pyr- rolidine is employed instead of (S)-3-(2-methanesulfonyloxyethyl)-5-(3,4-dichlorophenyl)-1-[(3-isopropoxyphenyl)acetyl)pyrrolidine.

EXAMPLE 8

Preparation of (S)-3-(2,5-dimethylphenyl)-1-[(3-isopropoxyphenyl)acetyl]-3-[2-[4-(piperidin-1-yl)piperidin-1-yl]ethyl]pyrrolidine

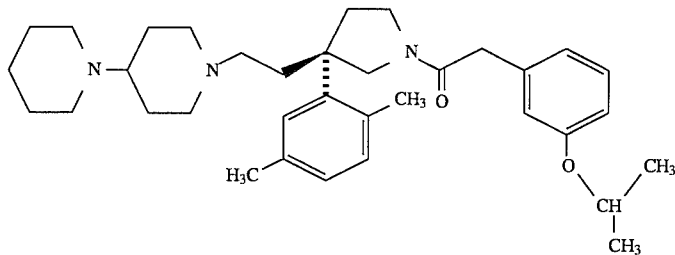

The title compound is prepared essentially as described in Example 1 except that (S)-3-(2-methanesulfonyloxyethyl)-3-(2,5-dimethylphenyl)-1-[3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 8a

Preparation of (S)-3-(3,4-diethoxyphenyl)-1-[(3-isopropoxyphenyl)acetyl]-3-[2-[4-(piperidin-1-yl)piperidin-1-yl]ethyl]pyrrolidine

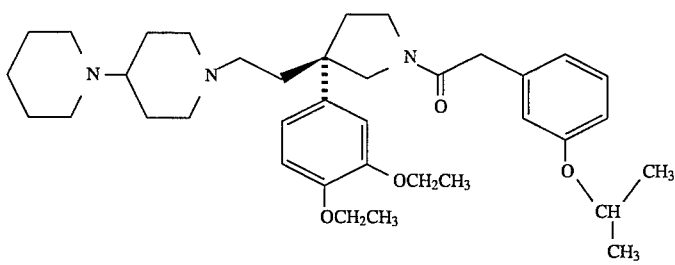

The title compound is prepared essentially as described in Example 1 except that (S)-3-(2-methanesulfonyloxyethyl)-3-(3,4-diethoxyphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 9

Preparation of (S)-3-[3-trifluoromethyl-4-trichloromethylphenyl]-1-[(3-isopropoxyphenyl)acetyl]-3-[2-[4-(piperidin-1-yl)piperidin-1-yl]ethyl]pyrrolidine

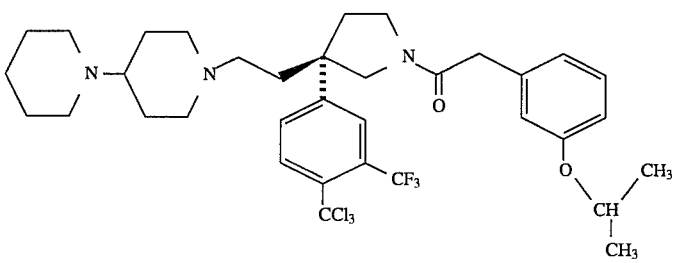

The title compound is prepared essentially as described in Example 1 except that (S)-3-(2-methanesulfonyloxyethyl)-3-[3-trifluoromethyl-4-trichloromethylphenyl]-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 10

Preparation of (S)-3-(3,4-diethylphenyl)-1-[(3-isopropoxyphenyl)acetyl]-3-[2-[4-(piperidin-1-yl)piperidin-1-yl]ethyl]pyrrolidine

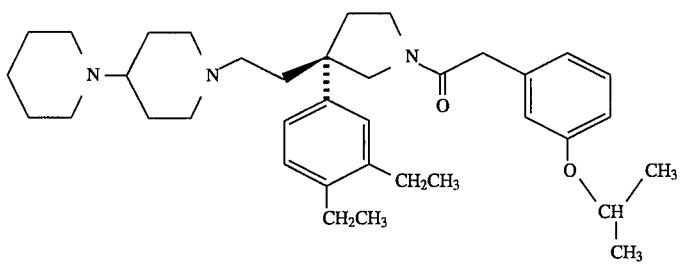

The title compound is prepared essentially as described in Example 1 except that (S)-3-(2-methanesulfonyloxyethyl)-3-(3,4-diethylphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 11

Preparation of (S)-3-(3,4-dichlorophenyl)-1-[(3-isopropoxyphenyl)acetyl]-3-[2-(4-cyclohexylpiperazin-1-yl)ethyl]pyrrolidine

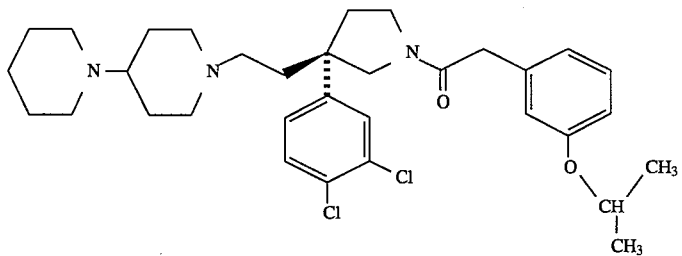

In 30 ml of acetonitrile (S)-3-(2-methanesulfonyloxyethyl)-3-(3,4-dichlorophenyl)-1-[(3-isopropoxyphenyl)acetyl)pyrrolidine (3.17 g), prepared as described, Supra, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 12

Preparation of (S)-3-[3,4-bis(trichloromethyl)phenyl]-1-[(3-isopropoxyphenyl)acetyl]-3-[2-(4-cyclohexylpiperazin-1-yl)ethyl]pyrrolidine

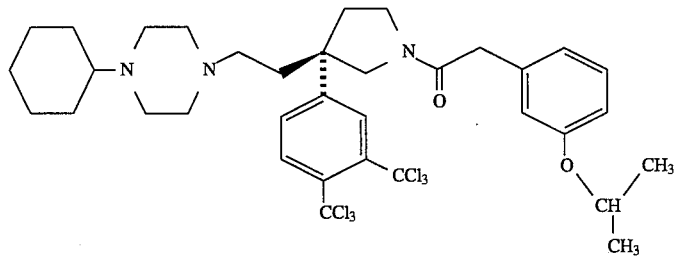

The title compound is prepared essentially as described in Example 11 except that (S)-3-(2-methanesulfonyloxyethyl)-3-[3,4-bis(trichloromethyl)phenyl]-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 13

Preparation of (S)-3-(3,4-dimethylphenyl)-1-[(3-isopropoxyphenyl)acetyl]-3-[2-(4-cyclohexylpiperazin-1-yl)ethyl]pyrrolidine

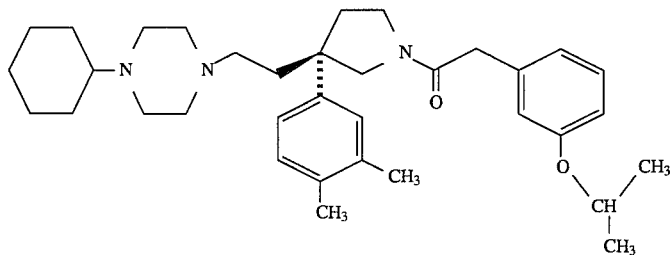

The title compound is prepared essentially as described in Example 11 except that (S)-3-(2-methanesulfonyloxyethyl)-3-(3,4-dimethylphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 13a

Preparation of (S)-3-(4-methylphenyl)-1-[(3-isopropoxyphenyl)acetyl]-3-[2-(4-cyclohexylpiperazin-1-yl)ethyl]pyrrolidine

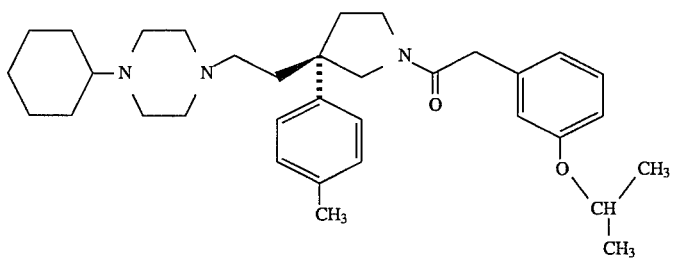

The title compound is prepared essentially as described in Example 11 except that (S)-3-(2-methanesulfonyloxyethyl)-3-(4-methylphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 14

Preparation of (S)-3-(3,4-dimethoxyphenyl)-1-isopropoxyphenyl)acetyl]-3-[2-(4-cyclohexylpiperazin-1-yl)ethyl]pyrrolidine

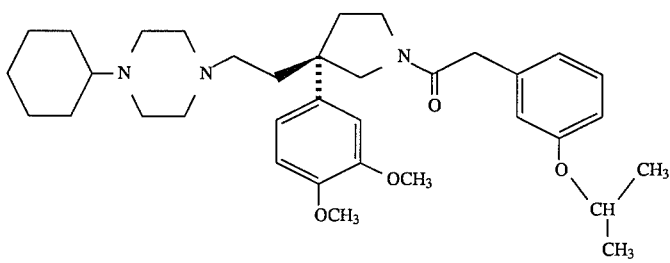

The title compound is prepared essentially as described in Example 11 except that (S)-3-(2-methanesulfonyloxyethyl)-3-(3,4-dimethoxyphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 15

Preparation of (S)-3-(3-chlorophenyl)-1-[(3-isopropoxyphenyl)acetyl]-3-[2-(4-cyclohexylpiperazin-1-yl)ethyl]pyrrolidine

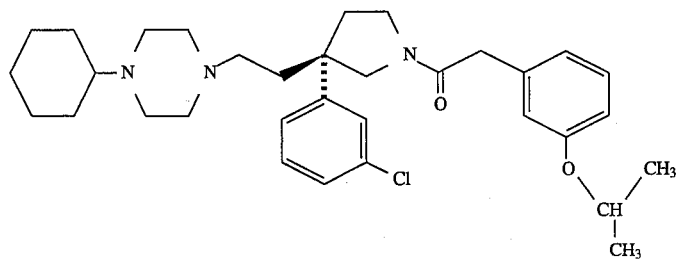

The title compound is prepared essentially as described in Example 11 except that (S)-3-(2-methanesulfonyloxyethyl)-3-(3-chlorophenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 16

Preparation of (S)-3-(3,4-difluorophenyl)-1-[(3-isopropoxyphenyl)acetyl]-3-[2-(4- cyclohexylpiperazin-1-yl)ethyl]pyrrolidine

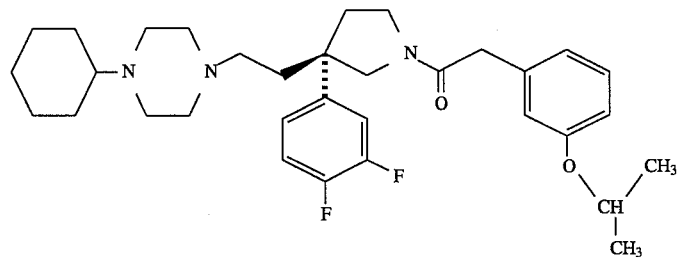

The title compound is prepared essentially as described in Example 11 except that (S)-3-(2-methanesulfonyloxyethyl)-3-(3,4-difluorophenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 17

Preparation of (S)-3-(2,5-dimethylphenyl)-1-[(3-isopropoxyphenyl)acetyl]-3-[2-(4-cyclohexylpiperazin-1-yl)ethyl]pyrrolidine

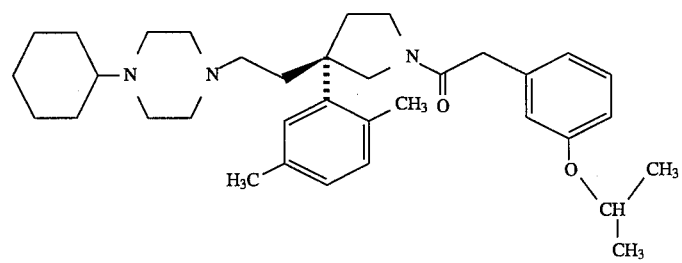

The title compound is prepared essentially as described in Example 11 except that (S)-3-(2-methanesulfonyloxyethyl-3-(2,5-dimethylphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 18

Preparation of (S)-3-(3,4-diethoxyphenyl)-1-[(3-isopropoxyphenyl)acetyl]-3-[2-(4-cyclohexylpiperazin-1-yl)ethyl]pyrrolidine

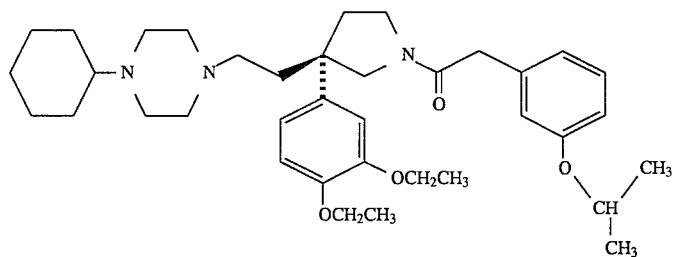

The title compound is prepared essentially as described in Example 11 except that (S)-3-(2-methanesulfonyloxyethyl)-3-(3,4-diethoxyphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 19

Preparation of (S)-3-[3,4-bis(trifluoromethyl)phenyl]-1-[(3-isopropoxyphenyl)acetyl]-3-[2-(4-cyclohexylpiperazin-1-yl)ethyl]pyrrolidine

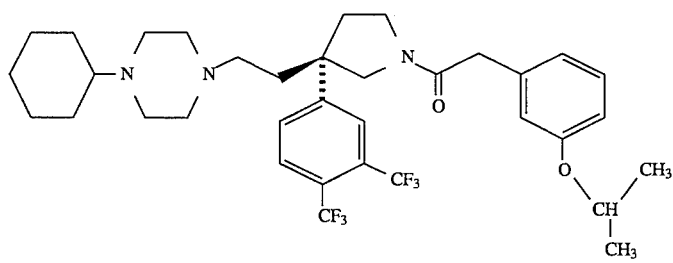

The title compound is prepared essentially as described in Example 11 except that (S)-3-(2-methanesulfonyloxyethyl)-3-[3,4-bis(trifluoromethyl)phenyl]-1-[(3-isopropoxyphenyl)acetyl]pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 20

Preparation of (S)-3-(3,4-diethylphenyl)-1-[(3-isopropoxyphenyl)acetyl]-3-[2-(4-cyclohexylpiperazin-1-yl)ethyl]pyrrolidine

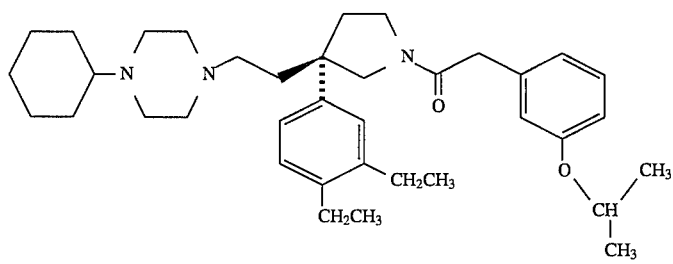

The title compound is prepared essentially as described in Example 11 except that (S)-3-(2-methanesulfonyloxyethyl)-3-(3,4-diethylphenyl)-1-[(3-isopropoxyphenyl)acetyl)pyrrolidine is employed instead of (S)-3-(2-methanesulfonyloxyethyl)-3-(3,4-dichlorophenyl)-1-[(3-isopropoxyphenyl)acetyl)pyrrolidine.

EXAMPLE 21

Preparation of (S)-3-(3,4-dichlorophenyl)-1-[[3,5-bis(trifluoromethyl)phenyl]acetyl]-3-[2-[4-(piperidin-1-yl)piperidin-1-yl]ethyl]pyrrolidine

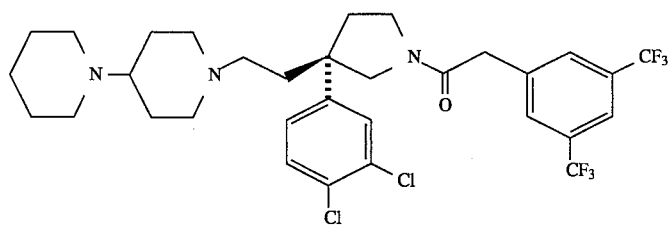

In 30 ml of acetonitrile (S)-3-(2-methanesulfonyloxyethyl)-3-(3,4-dichlorophenyl)-1-[[3,5-bis(trifluoromethyl)phenyl]acetyl]pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum an the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 22

Preparation of (S)-3-(3-trifluoromethyl-4-trichloromethylphenyl)-1-[[3,5-bis(trifluoromethyl)phenyl]acetyl]-3-[2-[4-(piperidin-1-yl)piperidin-1-yl]ethyl]pyrrolidine

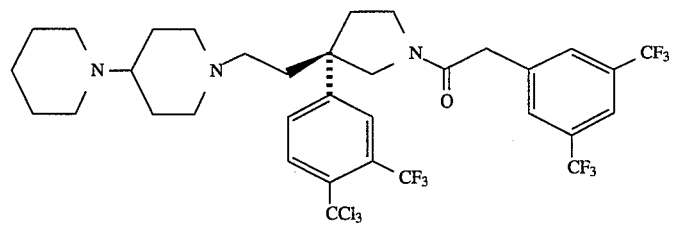

The title compound is prepared essentially as described in Example 2 1 except that (S)-3-(2-methanesulfonyloxyethyl)-3-(3-trifluoromethyl-4-trichloromethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 23

Preparation of (S)-3-(3,4-dimethylphenyl)-1-[[3,5-bis(trifluoromethyl)phenyl]acetyl]-3-[2-[4-(piperidin-1-yl)piperidin-1-yl]ethyl]pyrrolidine

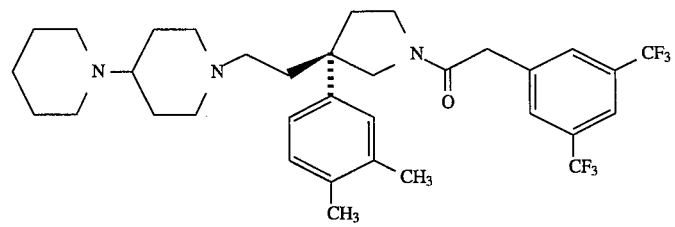

The title compound is prepared essentially as described in Example 21 except that (S)-3-(2-methanesulfonyloxyethyl)-3-(3,4-dimethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE.23a

Preparation of (S)-3-(4-methylphenyl)-1-[[3,5-bis-(trifluoromethyl)phenyl]acetyl]-3-[2-[4-(piperidin-1-yl)piperidin-1-yl]ethyl]pyrrolidine

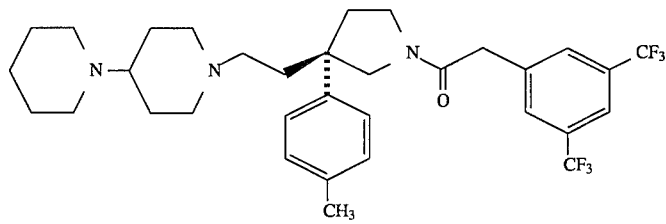

The title compound is prepared essentially as described in Example 21 except that (S)-3-(2-methanesulfonyloxyethyl)-3-(4-methylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 24

Preparation of (S)-3-(3,4-dimethoxyphenyl)-1-[[3,5-bis(trifluoromethyl)phenyl]acetyl]-3-[2-[4-(piperidin-1-yl)piperidin-1-yl]ethyl]pyrrolidine

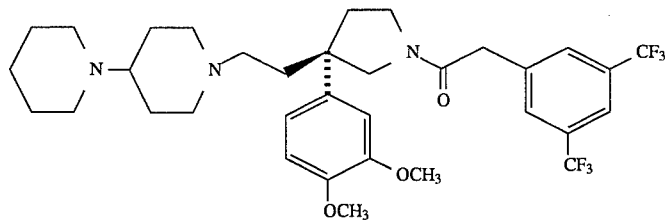

The title compound is prepared essentially as described in Example 21 except that (S)-3-(2-methanesulfonyloxyethyl)-3-(3,4-dimethoxyphenyl)-1-[[3,5-bis(trifluoromethyl)phenyl]acetyl]pyrrolidine is employed instead of (S)-3-(2-methanesulfonyloxyethyl)-3-(3,4dichlorophenyl)-1-[[3,5-bis(trifluoromethyl)phenyl]acetyl]pyrrolidine.

EXAMPLE 25

Preparation of (S)-3-(3-chlorophenyl)-1-[[3,5-bis-(trifluoromethyl)phenyl]acetyl]-3-[2-[4-(piperidin-1-yl)piperidin-1-yl]ethyl]pyrrolidine

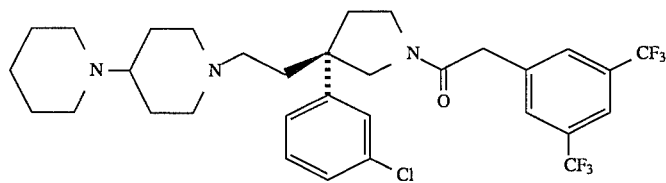

The title compound is prepared essentially as described in Example 21 except that (S)-3-(2-methanesulfonyloxyethyl)-3-(3-chlorophenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 26

Preparation of (S)-3-(3,4-difluorophenyl)-1-[[3,5-bis(trifluoromethyl)phenyl]acetyl]-3-[2-[4-(piperidin-1-yl)piperidin-1-yl]ethyl]pyrrolidine

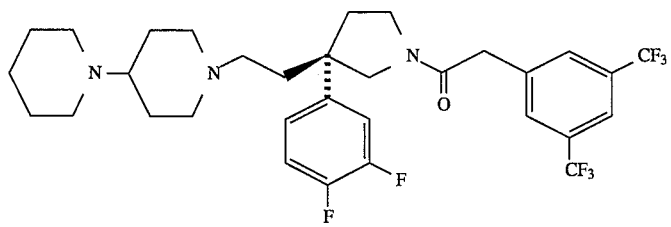

The title compound is prepared essentially as described in Example 21 except that (S)-3-(2-methanesulfonyloxyethyl)-3-(3,4-difluorophenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 27

Preparation of (S)-3-(2,5-dimethylphenyl)-1-[[3,5-bis(trifluoromethyl)phenyl]acetyl]-3-[2-[4-(piperidin-1-yl)piperidin-1-yl]ethyl]pyrrolidine

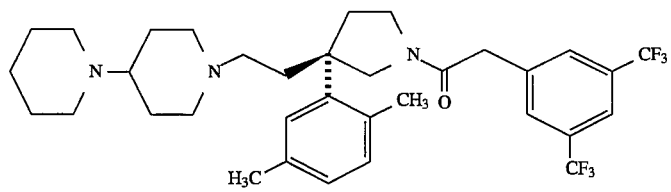

The title compound is prepared essentially as described in Example 21 except that (S)-3-(2-methanesulfonyloxyethyl)-3-(2,5-dimethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 28

Preparation of (S)-3-(3,4-diethoxyphenyl)-1-[[3,5-bis(trifluoromethyl)phenyl]acetyl]-3-[2-[4-(piperidin-1-yl)piperidin-1-yl]ethyl]pyrrolidine

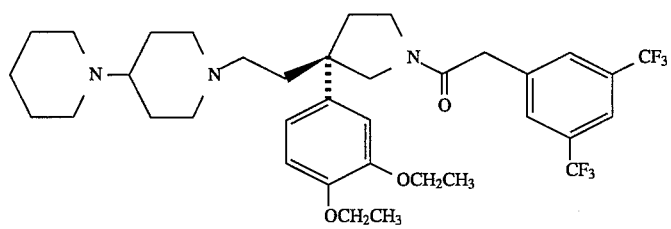

The title compound is prepared essentially as described in Example 21 except that (S)-3-(2-methanesulfonyloxyethyl)-3-(3,4-diethoxyphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 29

Preparation of (S)-3-[3,4-bis(trichloromethyl)phenyl]-1-[[3,5-bis(trifluoromethyl)phenyl]acetyl]-3-[2-[4-(piperidin-1-yl)piperidin-1-yl]ethyl]pyrrolidine

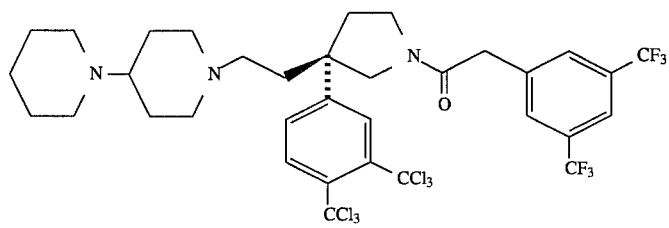

The title compound is prepared essentially as described in Example 21 except that (S)-3-(2-methanesulfonyloxyethyl)-3-[3,4-bis(trichloromethyl)phenyl]-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 30

Preparation of (S)-3-(3,4-diethylphenyl)-1-[[3,5-bis(trifluoromethyl)phenyl]acetyl]-3-[2-[4-(piperidin-1-yl)piperidin-1-yl]ethyl]pyrrolidine

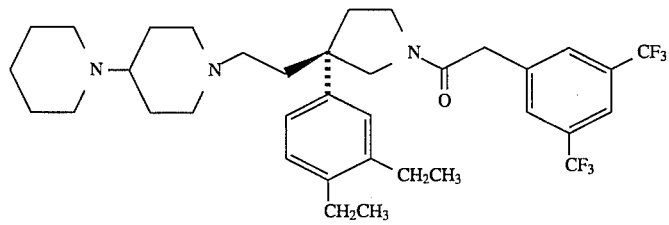

The title compound is prepared essentially as described in Example 21 except that (S)-3-(2-methanesulfonyloxyethyl)-3-(3,4-diethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 31

Preparation of (S)-3-(3,4-dichlorophenyl)-1-[[3,5-bis(trifluoromethyl)phenyl]acetyl]-3-[2-(4cyclohexylpiperazin-1-yl)ethyl]pyrrolidine

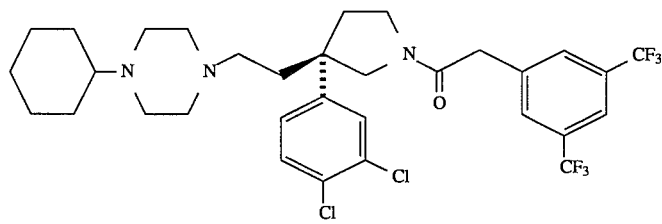

In 30 ml of acetonitrile (S)-3-(2-methanesulfonyloxyethyl)-3-(3,4-dichlorophenyl)-1-[[3,5-bis(trifluoromethyl)phenyl]acetyl]pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum an the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 32

Preparation of (S)-3-[3,4-bis(trifluoromethyl)phenyl]-1-[[3,5-bis(trifluoromethyl)phenyl]acetyl]-3-[2-(4-cyclohexylpiperazin-1-yl)ethyl]pyrrolidine

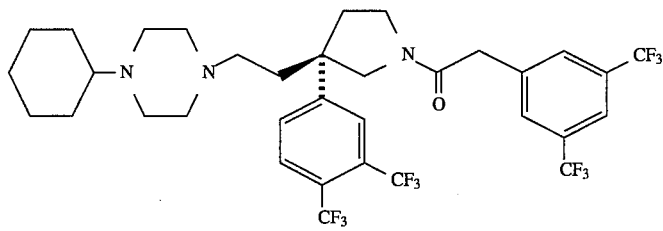

The title compound is prepared essentially as described in Example 31 except that (S)-3-(2-methanesulfonyloxyethyl)-3-[3,4-bis(trifluoromethyl)phenyl]-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 33

Preparation of (S)-3-(3,4-dimethylphenyl)-1-[[3,5-bis(trifluoromethyl)phenyl]acetyl]-3-[2-(4-cyclohexylpiperazin-1-yl)ethyl]pyrrolidine

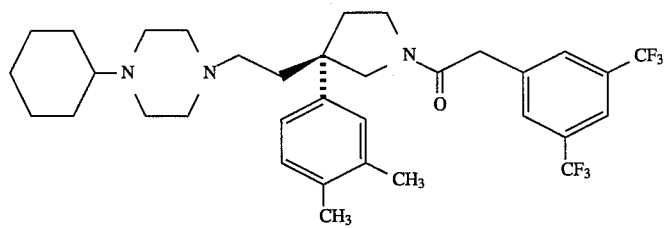

The title compound is prepared essentially as described in Example 31 except that (S)-3-(2-methanesulfonyloxyethyl)-3-(3,4-dimethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 33a

Preparation of (S)-3-(4-methylphenyl)-1-[[3,5-bis-(trifluoromethyl)phenyl]acetyl]-3-[2-(4-cyclohexylpiperazin-1-yl)ethyl]pyrrolidine

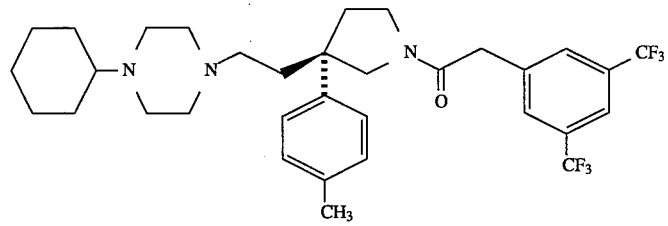

The title compound is prepared essentially as described in Example 31 except that (S)-3-(2-methanesulfonyloxyethyl)-3-(4-methylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 34

Preparation of (S)-3-(3,4-dimethoxyphenyl)-1-[[3,5-bis(trifluoromethyl)phenyl]acetyl]-3-[2-(4-cyclohexylpiperazin-1-yl)ethyl]pyrrolidine

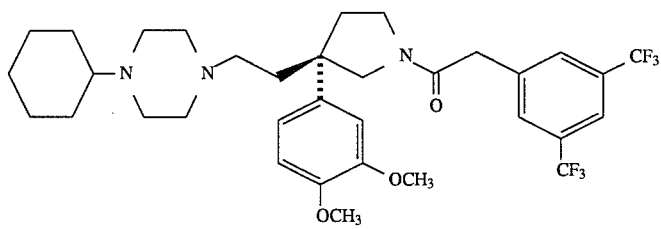

The title compound is prepared essentially as described in Example 31 except that (S)-3-(2-methanesulfonyloxyethyl)-3-(3,4-dimethoxyphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 35

Preparation of (S)-3-(3-chlorophenyl)-1-[[3,5-bis-(trifluoromethyl)phenyl]acetyl]-3-[2-(4-cyclohexylpiperazin-1-yl)ethyl]pyrrolidine

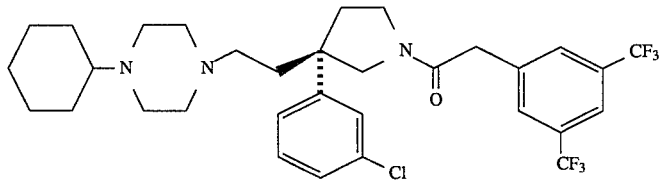

The title compound is prepared essentially as described in Example 31 except that (S)-3-(2-methanesulfonyloxyethyl-3-(3-chlorophenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 36

Preparation of (S)-3-(3,4-difluorophenyl)-1-[[3,5-bis(trifluoromethyl)phenyl]acetyl]-3-[2-(4-cyclohexylpiperazin-1-yl)ethyl]pyrrolidine

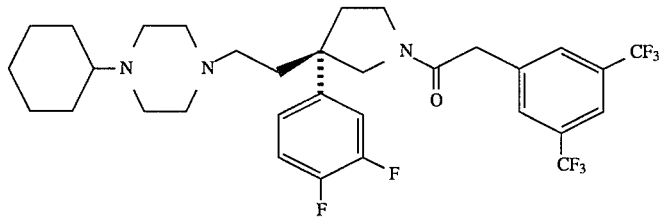

The title compound is prepared essentially as described in Example 31 except that (S)-3-(2-methanesulfonyloxyethyl)-3-(3,4-difluorophenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 37

Preparation of (S)-3-(2,5-dimethylphenyl)-1-[[3,5-bis(trifluoromethyl)phenyl]acetyl]-3-[2-(4-cyclohexylpiperazin-1-yl)ethyl]pyrrolidine

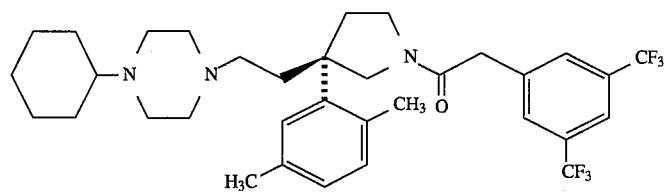

The title compound is prepared essentially as described in Example 31 except that (S)-3-(2-methanesulfonyloxyethyl)-3-(2,5-dimethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 38

Preparation of (S)-3-(3,4-diethoxyphenyl)-1-[[3,5-bis(trifluoromethyl)phenyl]acetyl]-3-[2-(4-cyclohexylpiperazin-1-yl)ethyl]pyrrolidine

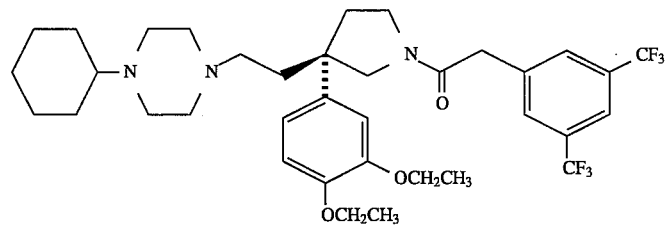

The title compound is prepared essentially as described in Example 31 except that (S)-3-(2-methanesulfonyloxyethyl)-3-(3,4-diethoxyphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 39

Preparation of (S)-3-[3,4-bis(trichloromethyl)phenyl]-1-[[3,5-bis(trifluoromethyl)phenyl]acetyl]-3-[2-(4-cyclohexylpiperazin-1-yl)ethyl]pyrrolidine

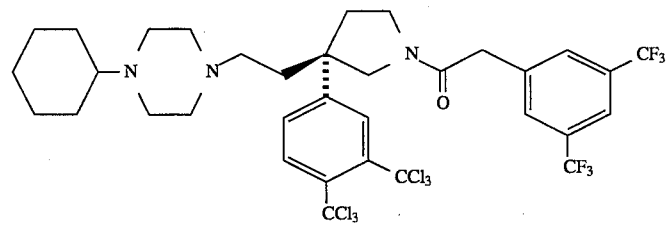

The title compound is prepared essentially as described in Example 31 except that (S)-3-(2-methanesulfonyloxyethyl)-3-[3,4-bis(trichloromethyl)phenyl]-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 40

Preparation of (S)-3-(3,4-diethylphenyl)-1-[[3,5-bis(trifluoromethyl)phenyl]acetyl]-3-[2-(4-cyclohexylpiperazin-1-yl)ethyl]pyrrolidine

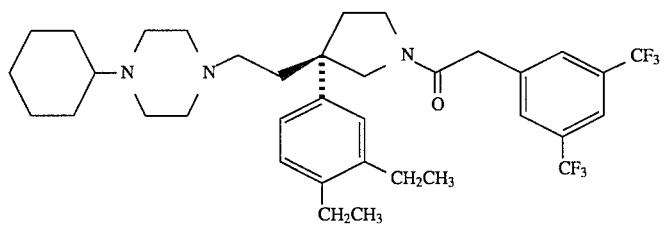

The title compound is prepared essentially as described in Example 31 except that (S)-3-(2-methanesulfonyloxyethyl)-3-(3,4-diethylphenyl)-1-[[3,5-bis(trifluoromethyl)phenyl]acetyl]pyrrolidine is employed instead of (S)-3-(2-methanesulfonyloxyethyl)-3-(3,4-dichlorophenyl)-1-[[3,5-bis(trifluoromethyl)phenyl]acetyl]pyrrolidine.

EXAMPLE 41

Preparation of (S)-3-(3,4-dichlorophenyl)-1-[(2-chloro-6-fluorophenyl)acetyl]-3-[2-[4-(piperidin-1-yl)piperidin-1-yl]ethyl]pyrrolidine

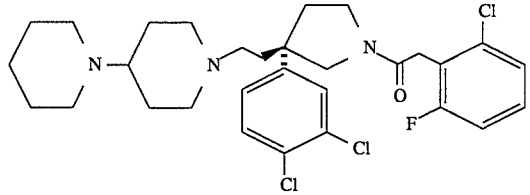

In 30 ml of acetonitrile (S)-3-(2-methanesulfonyloxyethyl)-3-(3,4-dichlorophenyl)-1-[[(2-chloro-6-fluorophenyl)acetyl]pyrrolidine (3.17 g), prepared as described, Supra, is mixed with an equimolar amount of 4-(piperidin-1-yl)piperidine. The reaction mixture is then heated to reflux and refluxed for about ten hours. The mixture is then concentrated under vacuum an the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 42

Preparation of (S)-3-[3,4-bis(trifluoromethyl)phenyl]-1-[(2-chloro-6-fluorophenyl)acetyl]-3-[2-[4-(piperidin-1-yl)piperidin-1-yl]ethyl]pyrrolidine

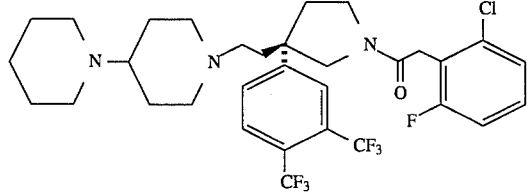

The title compound is prepared essentially as described in Example 41 except that (S)-3-(2-methanesulfonyloxyethyl)-3-[3,4-bis(trifluoromethyl)phenyl]-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 43

Preparation of (S)-3-(3,4-dimethylphenyl)-1-[(2-chloro-6-fluorophenyl)acetyl]-3-[2-[4-(piperidin-1-yl)piperidin-1-yl]ethyl]pyrrolidine

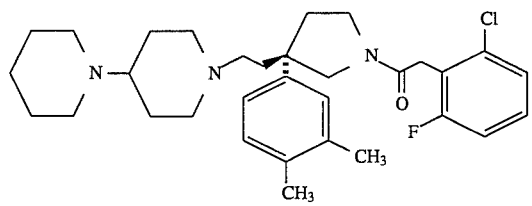

The title compound is prepared essentially as described in Example 41 except that (S)-3-(2-methanesulfonyloxyethyl)-3-(3,4-dimethylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 43a

Preparation of (S)-3-(4-methylphenyl)-1-[(2-chloro-6-fluorophenyl)acetyl]-3-[2-[4-(piperidin-1-yl)piperidin-1-yl]ethyl]pyrrolidine

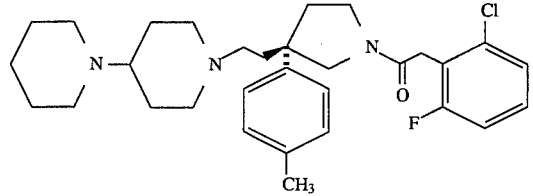

The title compound is prepared essentially as described in Example 41 except that (S)-3-(2-methanesulfonyloxyethyl)-3-(4-methylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 44

Preparation of (S)-3-(3,4-dimethoxyphenyl)-1-[(2-chloro-6-fluorophenyl)acetyl]-3-[2-[4-(piperidin-1-yl)piperidin-1-yl]ethyl]pyrrolidine

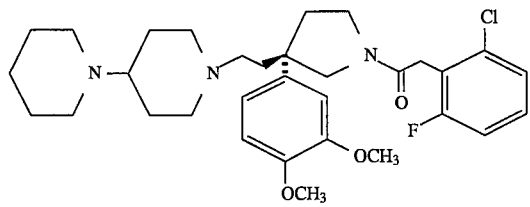

The title compound is prepared essentially as described in Example 41 except that (S)-3-(2-methanesulfonyloxyethyl)-3-(3,4-dimethoxyphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 45

Preparation of (S)-3-(3-chlorophenyl)-1-[(2-chloro-6-fluorophenyl)acetyl]-3-[2-[4-(piperidin-1-yl)piperidin-1-yl]ethyl]pyrrolidine

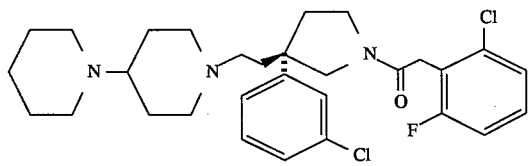

The title compound is prepared essentially as described in Example 41 except that (S)-3-(2-methanesulfonyloxyethyl)-3-(3-chlorophenyl)-1-[(2-chloro-6fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 46

Preparation of (S)-3-(3,4-difluorophenyl)-1-[(2-chloro-6-fluorophenyl)acetyl]-3-[2-[4-(piperidin-1-yl)piperidin-1-yl]ethyl]pyrrolidine

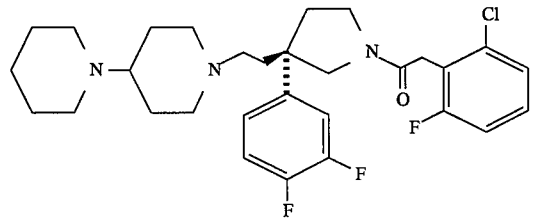

The title compound is prepared essentially as described in Example 41 except that (S)-3-(2-methanesulfonyloxyethyl)-3-(3,4-difluorophenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 47

Preparation of (s)-3-(2,5-dimethylphenyl)-1-[(2-chloro-6-fluorophenyl)acetyl]-3-[2-[4-(piperidin-1-yl)piperidin-1-yl]ethyl]pyrrolidine

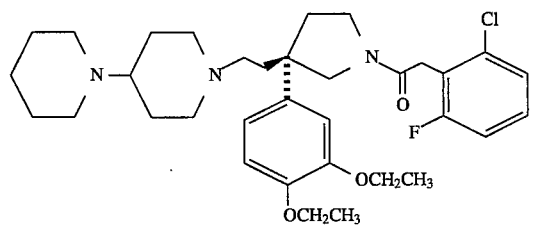

The title compound is prepared essentially as described in Example 41 except that (S)-3-(2-methanesulfonyloxyethyl)-3-(2,5-dimethylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 48

Preparation of (S)-3-(3,4-diethoxyphenyl)-1-[(2-chloro-6-fluorophenyl)acetyl]-3-[2-[4-(piperidin-1-yl)piperidin-1-yl]ethyl]pyrrolidine

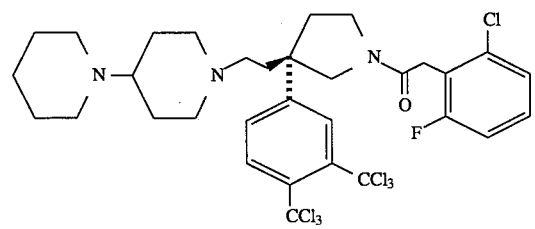

The title compound is prepared essentially as described in Example 41 except that (S)-3-(2-methanesulfonyloxyethyl)-3-(3,4-diethoxyphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 49

Preparation of (S)-3-[3,4-bis(trichloromethyl)phenyl]-1-[(2-chloro-6-fluorophenyl)acetyl]-3-[2-[4-(piperidin-1-yl)piperidin-1-yl]ethyl]pyrrolidine The title compound is prepared essentially as described in Example 41 except that (S)-3-(2-methanesulfonyloxyethyl-3-[3,4-bis(trichloromethyl)phenyl]-1-[(2-chloro-6fluorophenyl)acetyl]pyrrolidine is employed instead of (S)-3-(2-methanesulfonyloxyethyl)-3-(3,4-dichlorophenyl)-1-[(2-chloro-6- fluorophenyl)acetyl]pyrrolidine.

EXAMPLE 50

Preparation of (S)-3-(3,4-diethylphenyl)-1-[(2-chloro-6-fluorophenyl)acetyl]-3-[2-[4-(piperidin-1-yl)piperidin-1-yl]ethyl]pyrrolidine

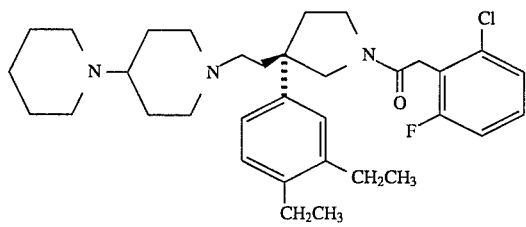

The title compound is prepared essentially as described in Example 41 except that (S)-3-(2-methanesulfonyloxyethyl)-3-(3,4-diethylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 51

Preparation of (S)-3-(3,4-dichlorophenyl)-1-[(2-chloro-6-fluorophenyl)acetyl]-3-[2-(4-cyclohexylpiperazin-1-yl)ethyl]pyrrolidine

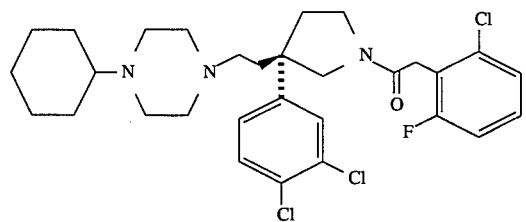

In 30 ml of acetonitrile (S)-3-(2-methanesulfonyloxyethyl)-3-(3,4-dichlorophenyl)-1-[(2-chloro-6-fluorophenyl)acetyl]pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum an the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 52

Preparation of (S)-3-[3,4-bis (trifluoromethyl)phenyl]-1-[(2-chloro-6-fluorophenyl)acetyl]-3-[2-(4-cyclohexylpiperazin-1-yl)ethyl]pyrrolidine

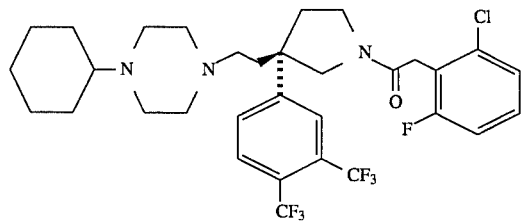

The title compound is prepared essentially as described in Example 51 except that (S)-3-(2-methanesulfonyloxyethyl)-3-[3,4-bis(trifluoromethyl)phenyl]-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 53

Preparation of (S)-3-(3,4-dimethylphenyl)-1-[(2-chloro-6-fluorophenyl)acetyl]-3-[2-(4-cyclohexylpiperazin-1-yl)ethyl]pyrrolidine

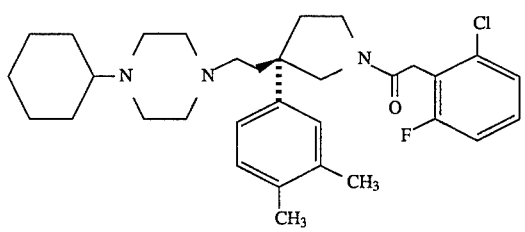

The title compound is prepared essentially as described in Example 51 except that (S)-3-(2-methanesulfonyloxyethyl)-3-(3,4-dimethylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 53a

Preparation of (S)-3-(4-methylphenyl)-1-[(2-chloro-6-fluorophenyl)acetyl]-3-[2-(4-cyclohexylpiperazin-1-yl)ethyl]pyrrolidine

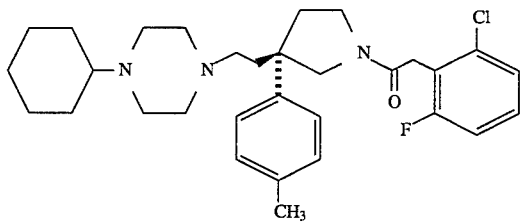

The title compound is prepared essentially as described in Example 51 except that (S)-3-(2-methanesulfonyloxyethyl-3-(4-methylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 54

Preparation of (S)-3-(3,4-dimethoxyphenyl)-1-[(2-chloro-6-fluorophenyl)acetyl]-3-[2-(4-cyclohexylpiperazin-1-yl)ethyl]pyrrolidine

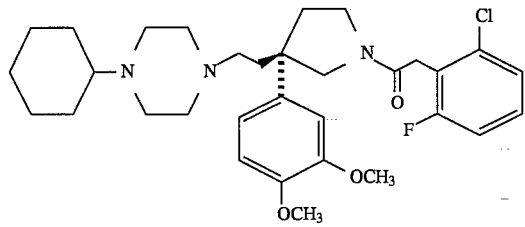

The title compound is prepared essentially as described in Example 51 except that (S)-3-(2-methanesulfonyloxyethyl)-3-(3,4-dimethoxyphenyl)-1-[(2-chloro-6-fluorophenyl)acetyl]pyrrolidine is employed instead of (S)-3-(2-methanesulfonyloxyethyl)-3-(3,4dichlorophenyl)-1-[(2-chloro-6-fluorophenyl)acetyl]pyrrolidine.

EXAMPLE 55

Preparation of (S)-3-(3-chlorophenyl)-1-[(2-chloro-6-fluorophenyl)acetyl]-3-[2-(4-cyclohexylpiperazin-1-yl)ethyl]pyrrolidine

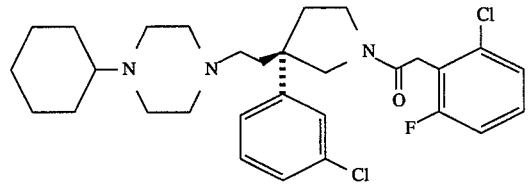

The title compound is prepared essentially as described in Example 51 except that (S)-3-(2-methanesulfonyloxyethyl)-3-(3-chlorophenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 56

Preparation of (S)-3-(3,4-difluorophenyl)-1-[(2-chloro-6-fluorophenyl)acetyl]-3-[2-(4-cyclohexylpiperazin-1-yl)ethyl]pyrrolidine

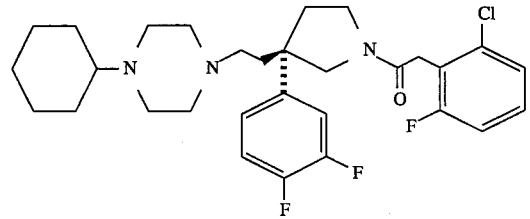

The title compound is prepared essentially as described in Example 51 except that (S)-3-(2-methanesulfonyloxyethyl)-3-(3,4-difluorophenyl)-1-[2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 57

Preparation of (S)-3-(2,5-dimethylphenyl)-1-[(2-chloro-6-fluorophenyl)acetyl]-3-[2-(4-cyclohexylpiperazin-1-yl)ethyl]pyrrolidine

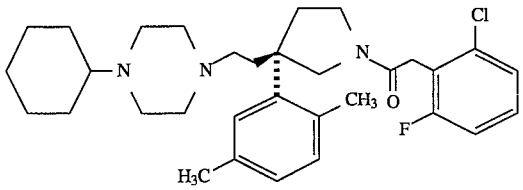

The title compound is prepared essentially as described in Example 51 except that (S)-3-(2-methanesulfonyloxyethyl)-3-(2,5-dimethylphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 58

Preparation of (S)-3-(3,4-diethoxyphenyl)-1-[(2-chloro-6-fluorophenyl)acetyl]-3-[2-(4-cyclohexylpiperazin-1-yl)ethyl]pyrrolidine

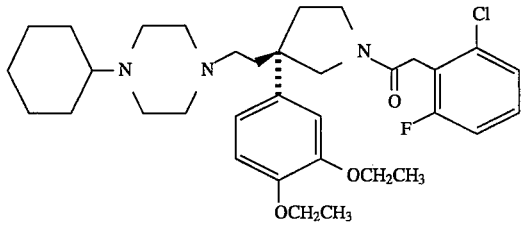

The title compound is prepared essentially as described in Example 51 except that (S)-3-(2-methanesulfonyloxyethyl)-3-(3,4-diethoxyphenyl)-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 59

Preparation of (S)-3-[3,4-bis(trichloromethyl)phenyl]-1-[(2-chloro-6-fluorophenyl)acetyl]-3-[2-(4-cyclohexylpiperazin-1-yl)ethyl]pyrrolidine

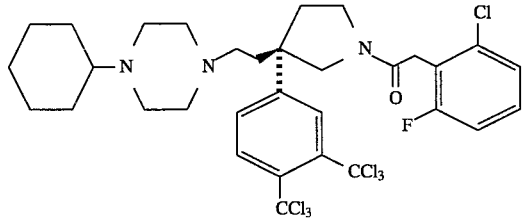

The title compound is prepared essentially as described in Example 51 except that (S)-3-(2-methanesulfonyloxyethyl)-3-[3,4-bis(trichloromethyl)phenyl]-1-[(2-chloro-6-fluorophenyl)acetyl]pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 60

Preparation of (S)-3-(3,4-diethylphenyl)-1-[(2-chloro-6-fluorophenyl)acetyl]-3-[2-(4-cyclohexylpiperazin-1-yl)ethyl]pyrrolidine

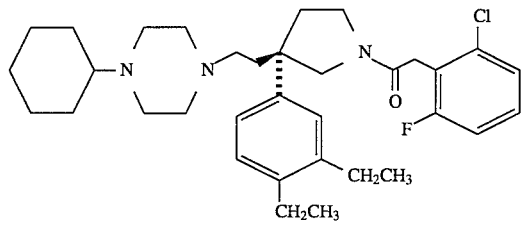

The title compound is prepared essentially as described in Example 51 except that (S)-3-(2-methanesulfonyloxyethyl)-3-(3,4-diethylphenyl)-1-[(2-chloro-6-fluorophenyl)acetyl] pyrrolidine is employed instead of (S)-3-(2-methanesulfonyloxyethyl)-3-(3,4-dichlorophenyl)-1-[(2-chloro-6-fluorophenyl)acetyl]pyrrolidine.

EXAMPLE 61

Preparation of (S)-3-(3,4-dichlorophenyl)-1-[(2-methoxyphenyl)acetyl]-3-[2-[4-(piperidin-1-yl)piperidin-1-yl]ethyl]pyrrolidine

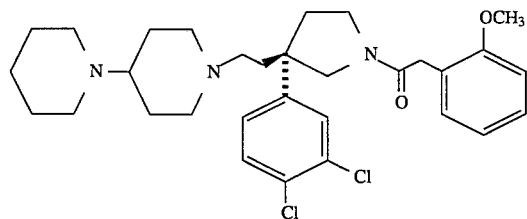

In 30 ml of acetonitrile (S)-3-(2-methanesulfonyloxyethyl)-3-(3,4-dichlorophenyl)-1-[(2-methoxyphenyl)acetyl)pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 62

Preparation of (S)-3-(3,4-dichlorophenyl)-1-[(2-methoxyphenyl)acetyl]-3-[2-(4-cyclohexylpiperazin-1-yl)ethyl]pyrrolidine

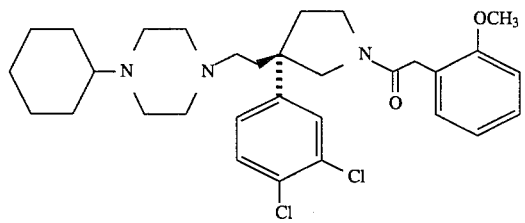

In 30 ml of acetonitrile (S)-3-(2-methanesulfonyloxyethyl)-3-(3,4-dichlorophenyl)-1-[(2-methoxyphenyl)acetyl)pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 63

Preparation of (S)-3-(3,4-dichlorophenyl)-1-[(2-methoxyphenyl)acetyl]-3-[2-[4-(piperidin-1-yl)piperidin-1-yl]ethyl]pyrrolidine

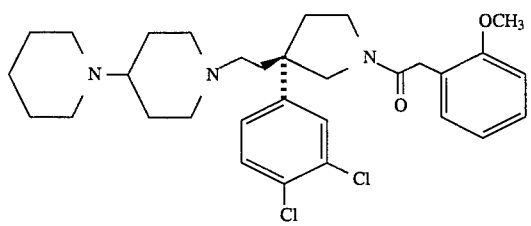

In 30 ml of acetonitrile (S)-3-(2-methanesulfonyloxyethyl)-3-(3,4-dichlorophenyl)-1-[(2-methoxyphenyl)acetyl] pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 64

Preparation of (S)-3-(3,4-dichlorophenyl)-1-[(2-methoxyphenyl)acetyl]-3-[2-(4-cyclohexylpiperazin-1-yl)ethyl]pyrrolidine

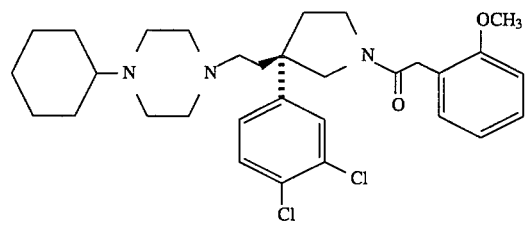

In 30 ml of acetonitrile (S)-3-(2-methanesulfonyloxyethyl)-3-(3,4-dichlorophenyl)-1-[(2-methoxyphenyl)acetyl] pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, fol-

EXAMPLE 65

Preparation of (S)-3-(3,4-dichlorophenyl)-1-[(2-methoxyphenyl)acetyl]-3-[2-[4-(piperidin-1-yl)piperidin-1-yl]ethyl]pyrrolidine

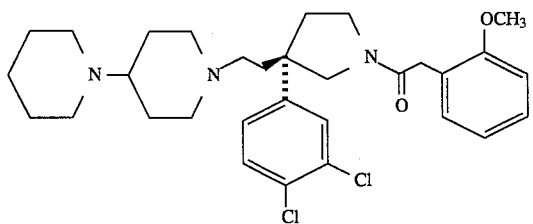

In 30 ml of acetonitrile (S)-3-(2-methanesulfonyloxyethyl)-3-(3,4-dichlorophenyl)-1-[(2-methoxyphenyl)acetyl]pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 66

Preparation of (S)-3-(3,4-dichlorophenyl)-1-[(2-methoxyphenyl)acetyl]-3-[2-(4-cyclohexylpiperazin-1-yl)ethyl]pyrrolidine

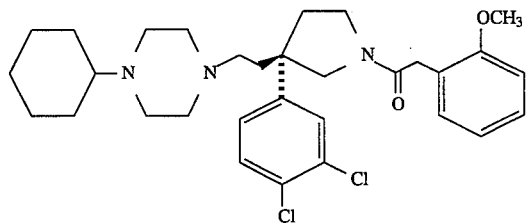

In 30 ml of acetonitrile (S)-3-(2-methanesulfonyloxyethyl)-3-(3,4-dichlorophenyl)-1-[(2-methoxyphenyl)acetyl]pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 67

Preparation of (S)-3-(3,4-dichlorophenyl)-1-[(2-methoxyphenyl)acetyl]-3-[2-[4-(piperidin-1-yl)piperidin-1-yl]ethyl]pyrrolidine

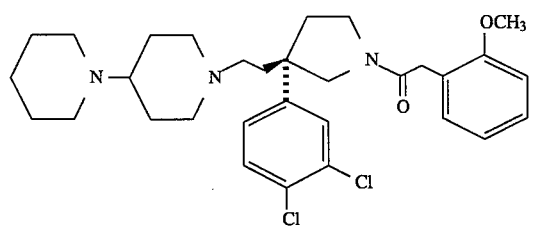

In 30 ml of acetonitrile (S)-3-(2-methanesulfonyloxyethyl)-3-(3,4-dichlorophenyl)-1-[(2-methoxyphenyl)acetyl)pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 68

Preparation of (R)-3-(3,4-dichlorophenyl)-1-[(3-isopropoxyphenyl)acetyl]-3-[2-(4-cyclohexylpiperazin-1-yl)ethyl]pyrrolidine

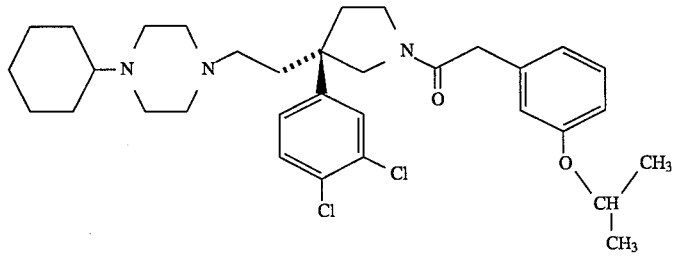

In 30 ml of acetonitrile (R)-3-(2-methanesulfonyloxyethyl)-3-(3,4-dichlorophenyl)-1-[(3-isopropoxyphenyl)acetyl)pyrrolidine (3.17 g), prepared as described, suora, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 69

Preparation of (R)-3-(3,4-dichlorophenyl)-1-[[3,5-bis(trifluoromethyl)phenyl]acetyl]-3-[2-[4-(piperidin-1-yl)piperidin-1-yl]ethyl]pyrrolidine

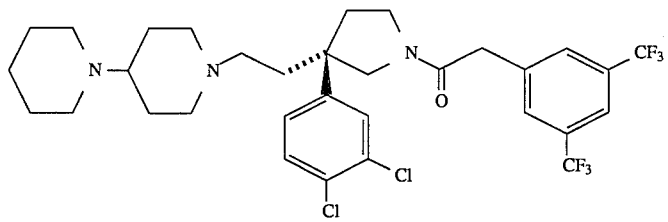

In 30 ml of acetonitrile (R)-3-(2-methanesulfonyloxyethyl)-3-(3,4-dichlorophenyl)-1-[[3,5-bis(trifluoromethyl)phenyl]acetyl]pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 70

Preparation of (R)-3-(3,4-dichlorophenyl)-1-[[3,5-bis(trifluoromethyl)phenyl]acetyl]-3-[2-(4-cyclohexylpiperazin-1-yl)ethyl]pyrrolidine

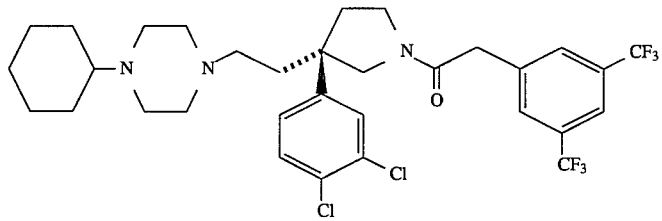

In 30 ml of acetonitrile (R)-3-(2-methanesulfonyloxyethyl)-3-(3,4-dichlorophenyl)-1-[[3,5-bis(trifluoromethyl)phenyl]acetyl]pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 71

Preparation of (R)-3-(3,4-dichlorophenyl)-1-[(2-chloro-6-fluorophenyl)acetyl]-3-[2-[4-(piperidin-1-yl)piperidin-1-yl]ethyl]pyrrolidine

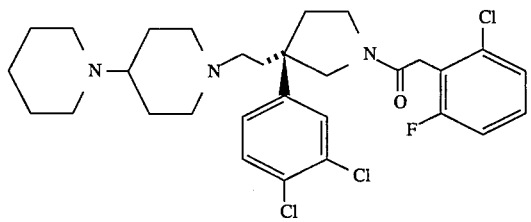

In 30 ml of acetonitrile (R)-3-(2-methanesulfonyloxyethyl)-3-(3,4-dichlorophenyl)-1-[(2-chloro-6-fluorophenyl)acetyl]pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 72

Preparation of (R)-3-(3,4-dichlorophenyl)-1-[(2-chloro-6-fluorophenyl)acetyl]-3-[2-(4-cyclohexylpiperaz in-1-yl)ethyl]pyrrolidine

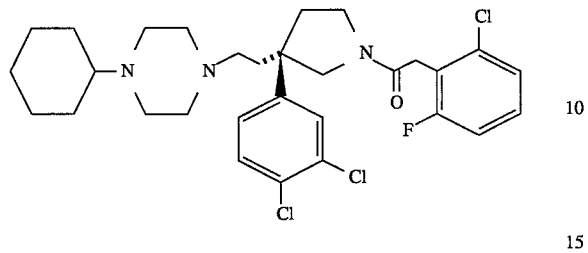

In 30 ml of acetonitrile (R)-3-(2-methanesulfonyloxyethyl)-3-(3,4-dichlorophenyl)-1-[(2-chloro-6-fluorophenyl)acetyl]pyrrolidine (3.17 g), prepared as described, supra, is mixed with an equimolar amount of 1-cyclohexylpiperazine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 73

Preparation of (S)-3-(1-naphthyl)-1-[(3-isopropoxyphenyl)acetyl]-3-[2-[4-(piperidin-1-yl)piperidin-1-yl]ethyl]pyrrolidine

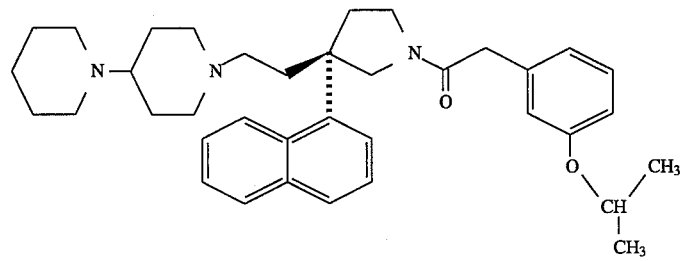

In 30 ml of acetonitrile (S)-3-(2-methanesulfonyloxyethyl)-3-(1-naphthyl)-1-[(3-isopropoxyphenyl)acetyl)pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum an the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 74

Preparation of (S)-3-(2-naphthyl)-1-[(3-isopropoxyphenyl)acetyl]-3-[2-[4-(piperidin-1-yl)piperidin-1-yl]ethyl]pyrrolidine

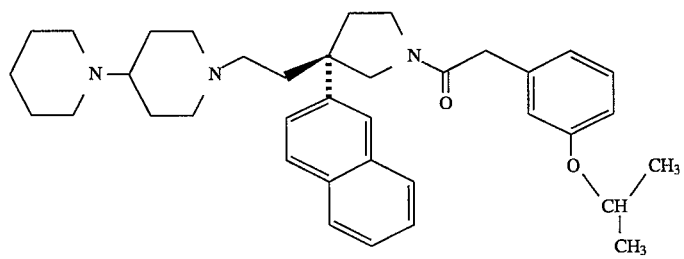

The title compound is prepared essentially as described in Example 73 except that (S)-3-(2-methanesulfonyloxyethyl)-3-(2-naphthyl)-1-[(3-isopropoxyphenyl)acetyl)pyrrolidine is employed instead of (S)-3-(2-methanesulfonyloxyethyl)-3-(1-naphthyl)-1-[(3-isopropoxyphenyl)acetyl)pyrrolidine.

EXAMPLE 75

Preparation of (S)-3-(1-naphthyl)-1-(3-isopropoxy-benzoyl)-3-[2-[4-(piperidin-1-yl)piperidin-1-yl]ethyl]pyrrolidine

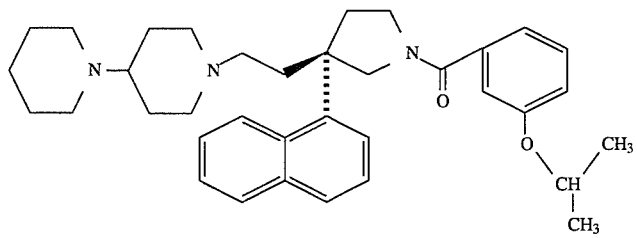

In 30 ml of acetonitrile (S)-3-(2-methanesulfonyloxyethyl)-3-(1-naphthyl)-1-(3-isopropoxybenzoyl)pyrrolidine (3.17 g), prepared as described, supra, is mixed with an equimolar amount of 4-(piperidin-1-yl)piperidine. The reaction mixture is then heated to reflux and refluxed for about ten hours. The mixture is then concentrated under vacuum an the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 76

Preparation of (S)-3-(2-naphthyl)-1-(3-isopropoxy-benzoyl)-3-[2-[4-(piperidin-1-yl)piperidin-1-yl]ethyl]pyrrolidine

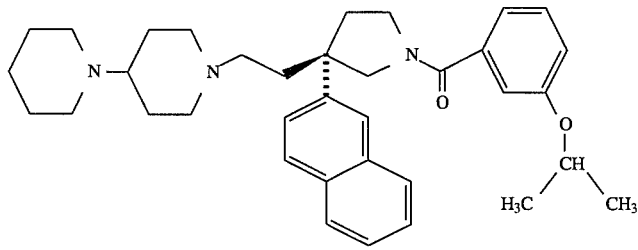

The title compound is prepared essentially as described in Example 73 except that (S)-3-(2-methanesulfonyloxyethyl)-3-(2-naphthyl)-1-(3-isopropoxybenzoyl)pyrrolidine is employed instead of (S)-3(2-methanesulfonyloxyethyl)-3-(1-naphthyl)-1-[(3-isopropoxybenzoyl) pyrrolidine.

EXAMPLE 77

Preparation of (S)-3-(3,4-dichlorophenyl)-1-(2-methoxybenzoyl)-3-[2-[4-(piperidin-1-yl)piperidin-1-yl]ethyl]pyrrolidine

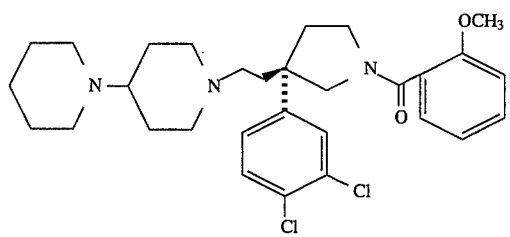

In 30 ml of acetonitrile (S)-3-(2-methanesulfonyloxyethyl)-3-(3,4-dichlorophenyl)-1-(2-methoxybenzoyl)pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 78

Preparation of (S)-3-(3,4-dimethoxyphenyl)-1-(2-methoxybenzoyl)-3-[2-[4-(piperidin-1-yl)piperidin-1-yl]ethyl]pyrrolidine

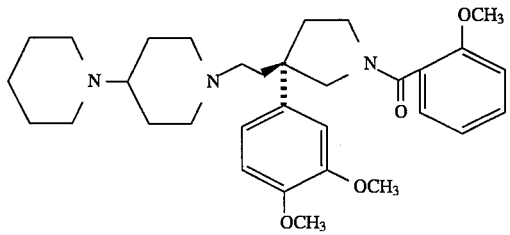

In 30 ml of acetonitrile (S)-3-(2-methanesulfonyloxyethyl)-3-(3,4-dimethoxyphenyl)-1-(2-methoxybenzoyl)pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 79

Preparation of (S)-3-(3,4-dichlorophenyl)-1-(2,4-dimethoxybenzoyl)-3-[2-[4-(piperidin-1-yl)piperidin-1-yl]ethyl]pyrrolidine

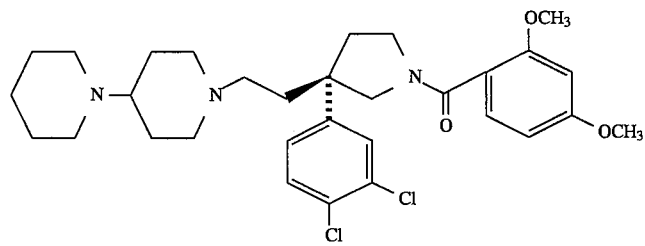

In 30 ml of acetonitrile (S)-3-(2-methanesulfonyloxyethyl)-3-(3,4-dichlorophenyl)-1-(2,4-dimethoxybenzoyl)pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 80

Preparation of (S)-3-(3,4-dimethoxyphenyl)-1-(2,4-dimethoxybenzoyl)-3-[2-[4-(piperidin-1-yl)piperidin-1-yl]ethyl]pyrrolidine

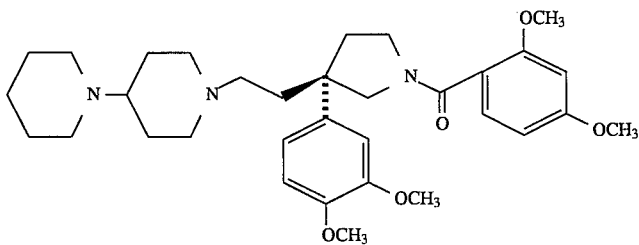

In 30 ml of acetonitrile (S)-3-(2-methanesulfonyloxyethyl)-3-(3,4-dimethoxyphenyl)-1-(2,4-methoxybenzoyl)pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 81

Preparation of (S)-3-(3,4-dichlorophenyl)-1-(3,4,5-trimethoxybenzoyl)-3-[2-[4-(piperidin-1-yl)piperidin-1-yl]ethyl]pyrrolidine

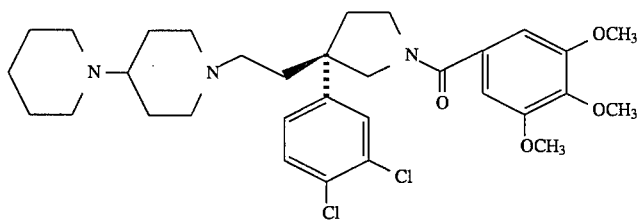

In 30 ml of acetonitrile (S)-3-(2-methanesulfonyloxyethyl)-3-(3,4-dichlorophenyl)-1-(3,4,5-trimethoxybenzoyl)pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

EXAMPLE 82

Preparation of (S)-3-(3,4-dimethoxyphenyl)-1-(3,4,5-trimethoxybenzoyl)-3-[2-[4-(piperidin-1-yl)piperidin-1-yl]ethyl]pyrrolidine

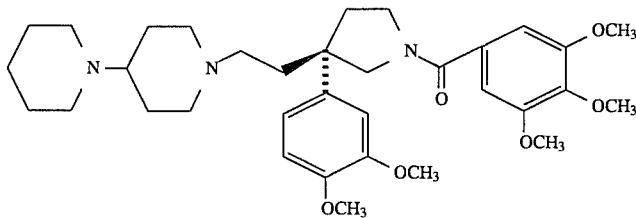

In 30 ml of acetonitrile (S)-3-(2-methanesulfonyloxyethyl)-3-(3,4-dimethoxyphenyl)-1-(3,4,5-trimethoxybenzoyl)pyrrolidine (3.17 g), prepared essentially as described, supra, is mixed with an equimolar amount of 4-(piperidin-1-yl)piperidine. The reaction mixture is then heated to reflux and refluxed for about ten hours. The mixture is then concentrated under vacuum and the residue is taken up in methylene chloride and washed with a 3N solution of hydrochloric acid, followed by a wash with brine. The organic fraction is dried over magnesium sulfate, filtered, and concentrated in vacuo. The residue precipitates from an acetone/diethyl ether mixture to give the desired title product.

In addition to the methods encompassed herein, the compounds of Formula I, as well as the intermediates of Formula II, may be prepared essentially as described in Patent Cooperation Treaty publication WO 94/26735, published Nov. 24, 1994.

The biological activity of the compounds of the present invention is evaluated employing an initial screening assay which rapidly and accurately measured the binding of the tested compound to known NK-1 and NK-2 receptor sites. Assays useful for evaluating tachykinin receptor antagonists are well known in the art. See, e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications*, 176:894–901 (1991).

NK-1 Receptor Binding Assay

Radioreceptor binding assays are performed using a derivative of a previously published protocol. D. G. Payan, et al., *Journal of Immunology*, 133:3260–3265 (1984). In this assay an aliquot of IM9 cells (1×10$^6$ cells/tube in RPMI 1604 medium supplemented with 10% fetal calf serum) is incubated with 20 pM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science*, 190:221–234 (1972); *Nature (London)*, 251:443–444 (1974); *Proceedings of the National Academy of Sciences (USA)*, 71:84–88 (1974). These cells are routinely cultured in RPMI 1640 supplemented with 50 μg/ml gentamicin sulfate and 10% fetal calf serum.

The reaction is terminated by filtration through a glass fiber filter harvesting system using filters previously soaked for 20 minutes in 0.1% polyethylenimine. Specific binding of labeled substance P is determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, are grown in 75 cm² flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures are dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells are pooled and centrifuged at 1,000 RPM for 10 minutes in a clinical centrifuge. Membranes are prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets are washed once using the above procedure. and the final pellets are resuspended in 100–120 ml 50 mM Tris buffer, pH 7.4, and 4 ml aliquots stored frozen at −70° C. The protein concentration of this preparation is 2 mg/ml.

For the receptor binding assay, one 4-ml aliquot of the CHO-hNK-2R membrane preparation is suspended in 40 ml of assay buffer containing 50 mM Tris, pH 7.4, 3 mM manganese chloride, 0.02% bovine serum albumin (BSA) and 4 µg/ml chymostatin. A 200 µl volume of the homogenate (40 µg protein) is used per sample. The radioactive ligand is [$^{125}$I]iodohistidyl-neurokinin A (New England Nuclear, NEX-252), 2200 Ci/mmol. The ligand is prepared in assay buffer at 20 nCi per 100 µl; the final concentration in the assay is 20 pM. Non-specific binding is determined using 1 µM eledoisin. Ten concentrations of eledoisin from 0.1 to 1000 nM are used for a standard concentration-response curve.

All samples and standards are added to the incubation in 10 µl dimethylsulfoxide (DMSO) for screening (single dose) or in 5 µl DMSO for IC$_{50}$ determinations. The order of additions for incubation is 190 or 195 µl assay buffer, 200 µl homogenate, 10 or 5 µl sample in DMSO, 100 µl radioactive ligand. The samples are incubated 1 hour at room temperature and then filtered on a cell harvester through filters which had been presoaked for two hours in 50 mM Tris buffer, pH 7.7, containing 0.5% BSA. The filter is washed 3 times with approximately 3 ml of cold 50 mM Tris buffer, pH 7.7. The filter circles are then punched into 12×75 mm polystyrene tubes and counted in a gamma counter.

As the compounds of Formula I are effective tachykinin receptor antagonists, these compounds are of value in the treatment of a wide variety of clinical conditions which are characterized by the presence of an excess of tachykinin. Thus, the invention provides methods for the treatment or prevention of a physiological disorder associated with an excess of tachykinins, which method comprises administering to a mammal in need of said treatment an effective amount of a compound of Formula I or a pharmaceutically acceptable salt, solvate or prodrug thereof. The term "physiological disorder associated with an excess of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative coliris, Crohn's disease, emesis, and irritable bowel syndrome; disorders of bladder function such as bladder detrusor hyper-reflexia and incontinence; artherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative coliris, Crohn's disease, emesis, and irritable bowel syndrome; incontinence; disorders of blood flow caused by vasodilation; and pain or nociception, for example, that attributable to or associated with any of the foregoing conditions or the transmission of pain in migraine.

Many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post parrum pain, angina pain, and genitourinary tract-related pain including cystiris.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; atherosclerosis; inflammatory conditions, such as inflammatory bowel disease, ulcerative coliris, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

Recent reports have demonstrated that the co-administration of an NK-1 antagonist and an NK-2 antagonist has a synergistic advantage over either alone. United Kingdom Patent Application GB 2,274,777 A, published Aug. 10, 1994. This line of reasonsing would suggest, therefore, that a compound of Formula I which has antagonist activity at both the NK-1 and NK-2 receptors, even though neither such activity is optimal when compared to the other compounds of Formula I, may be preferable to a compound having optimal activity at one or ther other receptor.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e,g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

I claim:

1. A compound of the formula

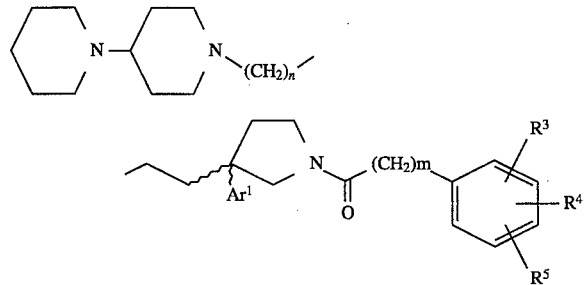

wherein:

n is 0–6;

m is 0–6;

$Ar^1$ is phenyl substituted with one or two moieties independently selected from the group consisting of hydrogen, halo, trifluoromethyl, trichloromethyl, $C_1$–$C_6$ alkyl, and $C_1$–$C_6$ alkoxy; or $Ar^1$ is naphthyl; and $R^3$, $R^4$, and $R^5$ are independently selected from the group consisting of hydrogen, halo, trifluoromethyl, $C_1$–$C_6$ alkyl, $C_1$–$C_6$ alkoxy, cyano, hydroxy, amino, —NHCONH$_2$, nitro, —CONH$_2$, $C_2$–$C_{10}$ alkenyl, $C_2$–$C_{10}$ alkynyl, $C_3$–$C_8$ cycloalkyl, $C_3$–$C_8$ cycloalkenyl, $C_3$–$C_8$ cycloalkoxy, $C_1$–$C_{10}$ alkylthio, $C_1$–$C_{10}$ alkylamino, $C_2$–$C_6$ alkanoyl, and $C_2$–$C_6$ alkanoyloxy; or a salt or solvate thereof.

2. A compound as claimed in claim 1 wherein $R^3$, $R^4$, and $R^5$ are independently selected from the group consisting of hydrogen, chloro, fluoro, methyl, ethyl, isopropyl, methoxy, ethoxy, isopropoxy, and trifluoromethyl, or a salt or solvate thereof.

3. A compound as claimed in claim 2 wherein $Ar^1$ is phenyl substituted with one or two groups independently selected from the group consisting of chloro, fluoro, methyl, ethyl, methoxy, ethoxy, isopropoxy, trifluoromethyl, and trichloromethyl, or a salt or solvate thereof.

4. A compound as claimed in claim 3 wherein n is 0, 1, or 2, or a salt or solvate thereof.

5. A compound as claimed in claim 4 wherein m is 0, or a salt or solvate thereof.

6. A compound as claimed in claim 5 selected from the group consisting of (S)-3-(3,4-dichlorophenyl)-1-(2-methoxybenzoyl)-3-[2-[4-(piperidin-1-yl)piperidin-1-yl]ethyl]pyrrolidine, (S)-3-(3,4-dimethoxyphenyl)-1-(2-methoxybenzoyl)-3-[2-[4-(piperidin-1-yl)piperidin-1-yl]ethyl]pyrrolidine, (S)-3-(3,4-dichlorophenyl)-1-(2,4-dimethoxybenzoyl)-3-[2-[4-(piperidin-1-yl)piperidin-1-yl]ethyl]pyrrolidine, (S)-3-(3,4-dimethoxyphenyl)-1-(2,4-dimethoxybenzoyl)-3-[2-[4-(piperidin-1-yl)piperidin-1-yl]ethyl]pyrrolidine, (S)-3-(3,4-dichlorophenyl)-1-(3,4,5-trimethoxybenzoyl)-3-[2-[4-(piperidin-1-yl)piperidin-1-yl]ethyl]pyrrolidine, and (S)-3-(3,4-dimethoxyphenyl)-1-(3,4,5-trimethoxybenzoyl)-3-[2-[4-(piperidin-1-yl)piperidin-1-yl]ethyl]pyrrolidine, or a salt or solvate thereof.

7. A compound as claimed in claim 4 wherein m is 1, or a salt or solvate thereof.

8. A pharmaceutical formulation comprising an effective amount of a compound of the formula

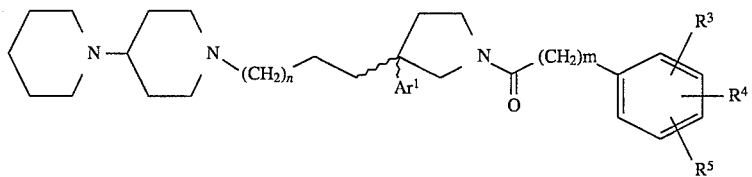

wherein:

n is 0–6;

m is 0–6;

Ar$^1$ is phenyl substituted with one or two moieties independently selected from the group consisting of hydrogen, halo, trifluoromethyl, trichloromethyl, $C_1$–$C_6$ alkyl, and $C_1$–$C_6$ alkoxy; or Ar$^1$ is naphthyl; and R$^3$, R$^4$, and R$^5$ are independently selected from the group consisting of hydrogen, halo, trifluoromethyl, $C_1$–$C_6$ alkyl, $C_1$–$C_6$ alkoxy, cyano, hydroxy, amino, —NHCONH$_2$, nitro, —CONH$_2$, $C_2$–$C_{10}$ alkenyl, $C_2$–$C_{10}$ alkynyl, $C_3$–$C_8$ cycloalkyl, $C_3$–$C_8$ cycloalkenyl, $C_3$–$C_8$ cycloalkoxy, $C_1$–$C_{10}$ alkylthio, $C_1$–$C_{10}$ alkylamino, $C_2$–$C_6$ alkanoyl, and $C_2$–$C_6$ alkanoyloxy;

or a pharmaceutically acceptable salt or solvate thereof, in combination with one or more pharmaceutically acceptable carriers, diluents, or excipients therefor.

9. A formulation as claimed in claim 8 employing a compound wherein R$^3$, R$^4$, and R$^5$ are independently selected from the group consisting of hydrogen, chloro, fluoro, methyl, ethyl, isopropyl, methoxy, ethoxy, isopropoxy, and trifluoromethyl, or a pharmaceutically acceptable salt or solvate thereof.

10. A formulation as claimed in claim 9 employing a compound wherein Ar$^1$ is phenyl substituted with one or two groups independently selected from the group consisting of chloro, fluoro, methyl, ethyl, methoxy, ethoxy, isopropoxy, trifluoromethyl, and trichloromethyl, or a pharmaceutically acceptable salt or solvate thereof.

11. A formulation as claimed in claim 10 employing a compound wherein n is 0, 1, or 2, or a pharmaceutically acceptable salt or solvate thereof.

12. A formulation as claimed in claim 11 employing a compound wherein m is 0, or a pharmaceutically acceptable salt or solvate thereof.

13. A formulation as claimed in claim 12 employing a compound selected from the group consisting of (S)-3-(3,4-dichlorophenyl)-1-(2-methoxybenzoyl)-3-[2-[4-(piperidin-1-yl)piperidin-1-yl]ethyl]pyrrolidine, (S)-3-(3,4-dimethoxyphenyl)-1-(2-methoxybenzoyl)-3-[2-[4-(piperidin-1-yl)piperidin-1-yl]ethyl]pyrrolidine, (S)-3-(3,4-dichlorophenyl)-1-(2,4-dimethoxybenzoyl)-3-[2-[4-(piperidin-1-yl)piperidin-1-yl]ethyl]pyrrolidine, (S)-3-(3,4-dimethoxyphenyl)-1-(2,4-dimethoxybenzoyl)-3-[2-[4-(piperidin-1-yl)piperidin-1-yl]ethyl]pyrrolidine, (S)-3-(3,4-dichlorophenyl)-1-(3,4,5-trimethoxybenzoyl)-3-[2-[4-(piperidin-1-yl)piperidin-1-yl]ethyl]pyrrolidine, and (S)-3-(3,4-dimethoxyphenyl)-1-(3,4,5-trimethoxybenzoyl)-3-[2-[4-(piperidin-1-yl)piperidin-1-yl]ethyl]pyrrolidine, or a pharmaceutically acceptable salt or solvate thereof.

14. A formulation as claimed in claim 11 employing a compound wherein m is 1, or a pharmaceutically acceptable salt or solvate thereof.

* * * * *